(12) United States Patent
Coelho et al.

(10) Patent No.: US 8,066,127 B2
(45) Date of Patent: Nov. 29, 2011

(54) INSTRUMENTALITY FOR SEQUESTERING LIQUIDS BASED ON DENSITY: METHOD AND APPARATUS

(75) Inventors: Philip H. Coelho, Sacramento, CA (US); Eric Sommer, El Dorado Hills, CA (US); Richard Klosinski, Carmichael, CA (US); Jim Hobbs, Carmichael, CA (US); Bruce Baker, Placerville, CA (US); Brian Malone, Elk Grove, CA (US)

(73) Assignee: ThermoGenesis Corp., Rancho Cordova, CA (US)

( * ) Notice: Subject to any disclaimer, the term of this patent is extended or adjusted under 35 U.S.C. 154(b) by 401 days.

(21) Appl. No.: 11/664,212

(22) PCT Filed: Aug. 16, 2005

(86) PCT No.: PCT/US2005/029288
§ 371 (c)(1),
(2), (4) Date: Aug. 5, 2008

(87) PCT Pub. No.: WO2006/038993
PCT Pub. Date: Apr. 13, 2006

(65) Prior Publication Data
US 2008/0311651 A1  Dec. 18, 2008

(51) Int. Cl.
*B01D 24/32* (2006.01)
*B04B 5/02* (2006.01)
*A61M 37/00* (2006.01)
*B04B 5/00* (2006.01)

(52) U.S. Cl. ............ 210/361; 210/782; 210/86; 210/91; 210/103; 210/362; 494/16; 494/20; 494/21; 494/37; 604/6.15; 604/403; 604/408; 604/410; 604/500

(58) Field of Classification Search .................. None
See application file for complete search history.

(56) References Cited

U.S. PATENT DOCUMENTS

| 4,120,448 A | 10/1978 | Cullis |
| 4,720,284 A | 1/1988 | McCarty |
| D314,824 S | 2/1991 | Moon |
| 5,674,173 A | 10/1997 | Hlavinka et al. |
| 5,723,050 A | 3/1998 | Unger et al. |

(Continued)

FOREIGN PATENT DOCUMENTS
WO   WO95/01842   1/1995

*Primary Examiner* — Krishnan S Menon
(74) *Attorney, Agent, or Firm* — Audrey A. Millemann; Bernhard Kreten; Weintraub Genshlea et al.

(57) ABSTRACT

An apparatus and method for collecting whole blood and then separating it into components for subsequent use or storage. A self-contained bag set is used to collect the sample, which may then be placed into a device adapted to fit into a centrifuge for separation of components. Each component is then sequentially extracted according to density, with a sensor present in the device to control the operation of valves directing the collection of each component. The sensor may be reading one or more of the following characteristics: infrared, optics, density, weight, radioactive, fluorescence, color, magnetism, ultrasonic, capacitance wherein the characteristic is inherent in the blood and blood component or is an additive. Each component may then be separated into its own storage container. The preferred sensors include optics and weight. Besides blood density separation, the device may contain a solution including cells, proteins, subcellular particles or viruses which may be mixed with affinity media or antibodies prior to separation.

2 Claims, 32 Drawing Sheets

U.S. PATENT DOCUMENTS

| | | |
|---|---|---|
| 5,792,038 A | 8/1998 | Hlavinka |
| 5,921,050 A | 7/1999 | Munch et al. |
| 6,315,706 B1 | 11/2001 | Unger et al. |
| 6,348,031 B1 | 2/2002 | Unger et al. |
| 6,652,475 B1 | 11/2003 | Sahines et al. |
| 2002/0082153 A1* | 6/2002 | Jorgensen et al. ............... 494/2 |
| 2004/0104182 A1* | 6/2004 | Holmes et al. ............... 210/787 |

* cited by examiner

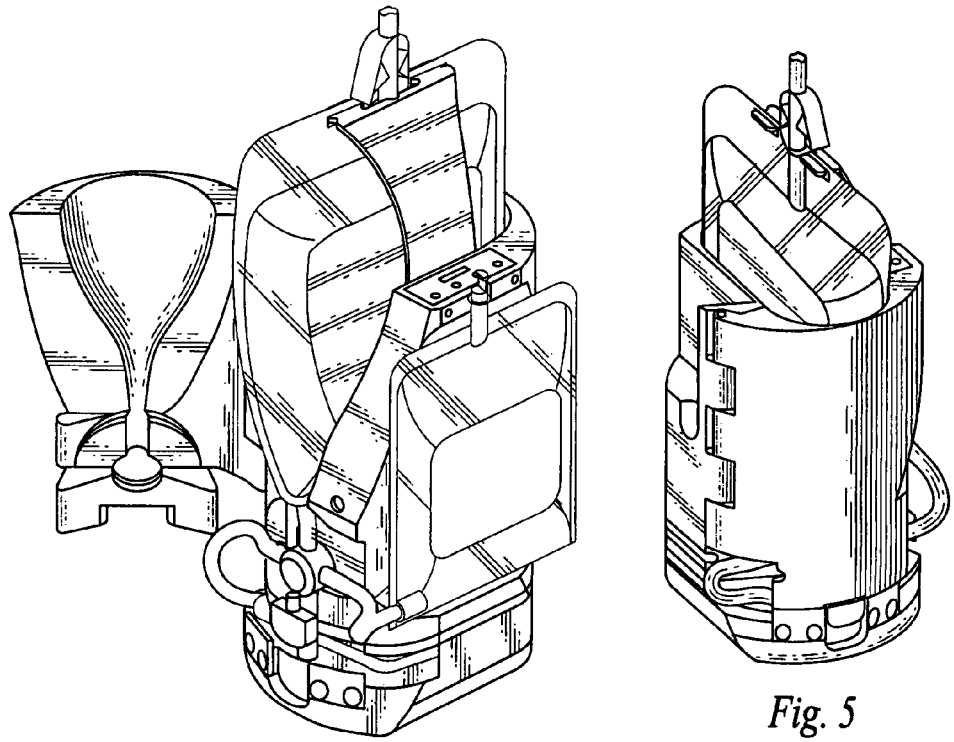
Fig. 4
Fig. 5
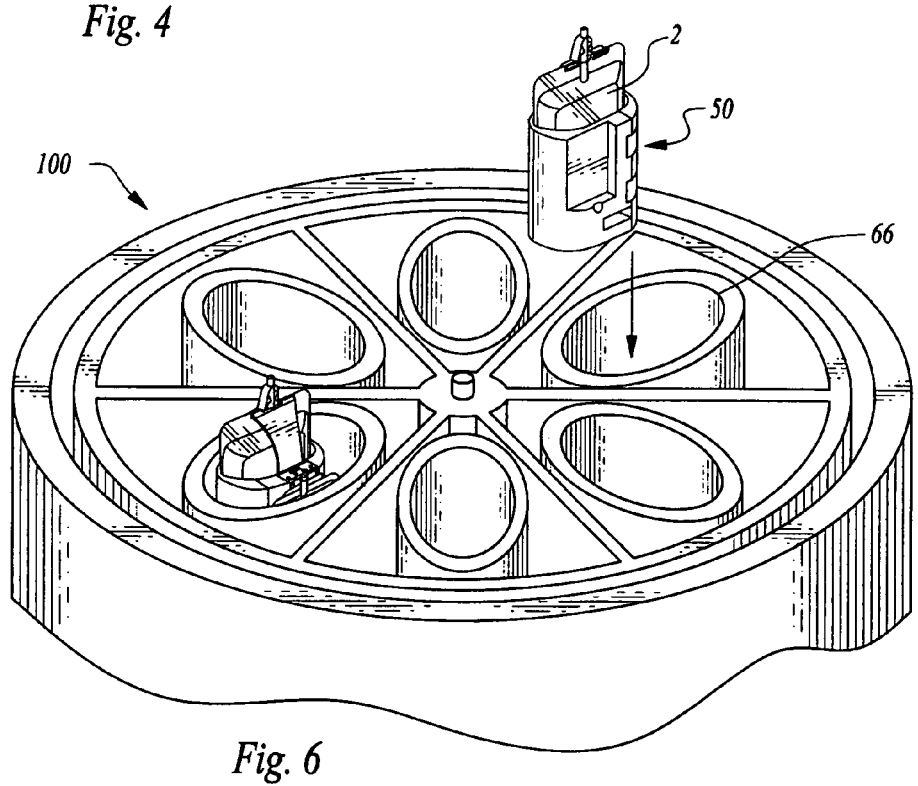
Fig. 6

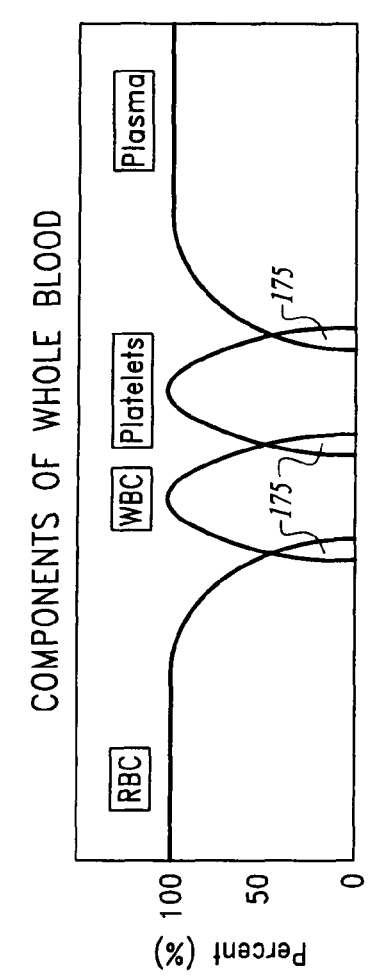
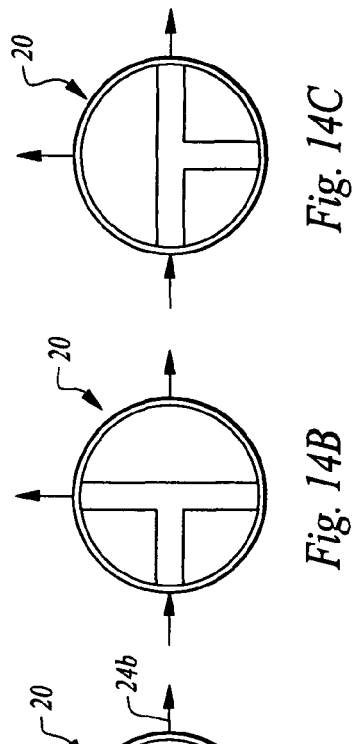
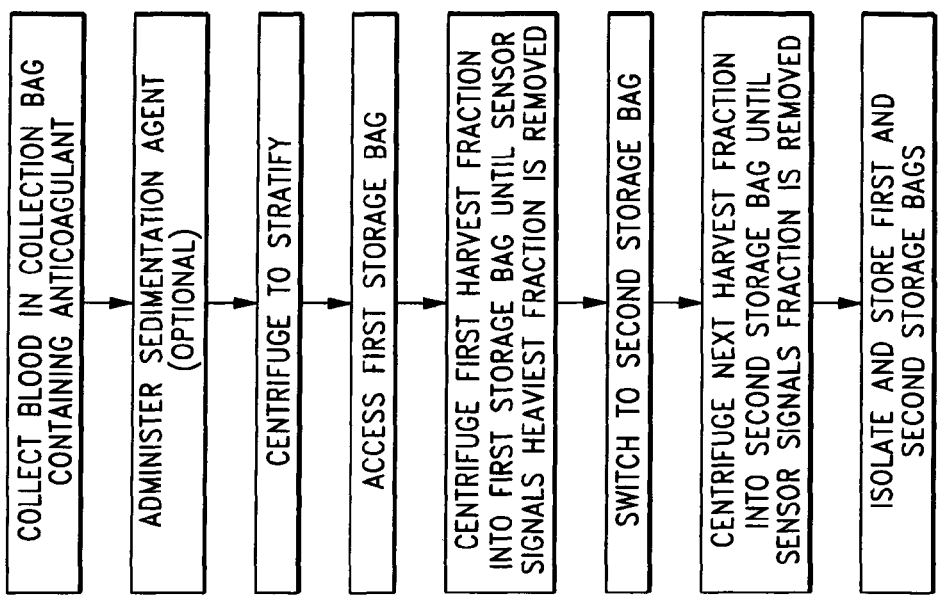
Fig. 13
Fig. 14A   Fig. 14B   Fig. 14C
Fig. 12

INSTRUMENTALITY FOR SEQUESTERING LIQUIDS BASED ON DENSITY:METHOD AND APPARATUS

CROSS-REFERENCE TO RELATED APPLICATION

This application is a national stage application based on PCT application no. PCT/US2005/029288 filed on. Aug. 16, 2005, which claimed priority to U.S. application Ser. No. 10/957,095 filed on Sep. 30, 2004, now U.S. Pat. No. 7,211,191.

FIELD OF THE INVENTION

The following invention relates generally to instrumentalities and methodologies in blood component separation. More specifically, the instant invention is directed to a method and apparatus for collecting a blood sample and subsequently separating the collected sample into constituent blood components for individual storage or use.

BACKGROUND OF THE INVENTION

Blood collection is always important, particularly in times of emergency (immediate use), but whole blood may only be stored for about 30 days before it is "outdated". For long term storage, the ability to separate the whole blood into its major components (white blood cells, platelets, red blood cells and plasma) is of paramount importance because the long term storage condition for each component is different in terms of temperature and storage media. The most important component separations occurring after collection is the separation of red blood cells (RBC), white blood cells (WBC), platelets, and plasma from one another. Within the WBC it is sometimes important to separate the granulocytes from the lymphocytes and monocytes. After separation and extraction of particular components, a fraction of the blood may be returned to the patient.

It is possible to separate the various components of whole blood either under or after centrifugation, due to their differing densities. Some prior art methods, such as that in U.S. Pat. No. 4,120,448, utilize a chamber connected to a centrifuge. The centrifuged blood separates in the chamber, and a plurality of collection means are positioned at various locations in the chamber corresponding to the areas where each component congregates, which is density-dependent.

The present (prior art) technique for sequestering white blood cells from whole blood: requires skilled technicians, is labor intensive in that it requires 16 steps conducted over the span of one hour, and produces inconsistent results because of the requirements placed on the technician in the exercise of technique. Most significantly, however, the 16 step present technique is "open"; that is, the blood product is processed in a manner that does not maintain the sterility of the product because the need to obtain samples or add sedimenting agents or cryoprotectants at the various stages of production can not be accomplished with allowing the outside environment access to the interior, meaning potential contamination of the product:

The 16 steps are:
1. Collect placental blood into collection bag (range 60-200 ml).
2. Add HES to collection bag (20% v/v).
3. Load collection bag into special centrifuge cup supports.
4. Centrifuge at 50 G for 13 min. to raise WBC from RBC (up to 6 units at one time).
5. Spike or sterile dock collection bag to expressor and processing bag set to scale.
6. Gently transfer collection bag to expressor and processing bag set to scale.
7. Express off WBC rich plasma and 10-15 ml of the top layer of RBC into processing bag—leaving excess RBC.
8. Remove collection bag with excess RBC.
9. Load processing bag set in special centrifuge cup supports.
10. Centrifuge processing bag set at 400 G for 10 min. (up to 6 units at one time).
11. Gently transfer processing bag to expressor.
12. Express off excess plasma leaving 20 ml WBC concentrate.
13. Remove excess plasma bag from processing set.
14. Add 5 ml cryoprotectant to WBC in processing bag at 4° C.
15. Transfer cryoprotected WBC to freezing bag.
16. Tube seal and separate freezing bag from processing bag.

The following prior art reflects the state of the art of which applicant is aware and is included herewith to discharge applicant's acknowledged duty to disclose relevant prior art. It is stipulated, however, that none of these references teach singly nor render obvious when considered in any conceivable combination the nexus of the instant invention as disclosed in greater detail hereinafter and as particularly claimed.

| PAT. NO. | ISSUE DATE | INVENTOR |
| --- | --- | --- |
| 4,120,448 | Oct. 17, 1978 | Cullis |
| 4,720,284 | Jan. 19, 1988 | McCarty |
| Des. 314,824 | Feb. 19, 1991 | Moon |
| 5,674,173 | Oct. 7, 1997 | Hlavinka et al. |
| 5,723,050 | Mar. 3, 1998 | Unger et al. |
| 5,792,038 | Aug. 11, 1998 | Hlavinka |
| 5,921,950 | Jul. 13, 1999 | Toavs et al. |
| 6,315,706 | Nov. 13, 2001 | Unger et al. |
| 6,348,031 | Feb. 19, 2002 | Unger et al. |
| 6,652,475 | Nov. 25, 2003 | Sahines et al. |
| WO95/01842 | Published: Jan. 15, 1995 | Unger |

The prior art references listed above but not specifically described teach other devices for blood processing and further catalog the prior art of which the applicant is aware. These references diverge even more starkly from the reference specifically distinguished above.

SUMMARY OF THE INVENTION

The present invention comprises a bag set that may be used to collect a whole blood sample from a source. Most significantly, the bag set defines a closed system in that once the blood is introduced, processing can occur outside a clean room or away from a sterile hood because access to any pathogens in the exterior environment is prevented. The bag set is then placed into a centrifuge for component separation. The whole blood processing bag, which may contain an anticoagulant such as CPD, ACD or CPD-A, contains at least one inlet and one outlet port connected to a plurality of component bags. The processing bag may optionally contain a sedimenting aid such as HES, but, unlike the prior art, such sedimenting aid is not required. Each component bag has a separate line leading from the whole blood processing bag, and each line can be clamped, tube-sealed and separated from the whole blood processing bag once a particular component bag has been filled.

In practice, the blood is collected and directed into an inlet port on the whole blood processing bag and the input line is clamped, sealed off, and separated from the whole blood processing bag. The whole blood processing bag, which is asymmetrically shaped, hangs in a bag set holder having a complementally shaped opening that closely contacts the bag at the bottom end, and an exterior of the bag set holder is adapted to fit in a conventional centrifuge cup or socket. The centrifuge is operated at varying G-forces to optimally separate the components. Once the components are separated by density in the whole blood processing bag, a servo motor is engaged to open a metering valve on the line leading from the processing bag to a bag that will contain the densest component. This allows the densest component to fill its particular storage bag, usually under centrifugation.

Applicant's process can be summarized in the following 7 or 8 steps which are performed over a span of 25 minutes, resulting in repeatable yields in excess of 90% of the lymphocytes and monocytes.

1. Collect placental blood into collection bag (range 60-200 ml).
2. Spike or sterile dock collection bag to bag processing set and transfer blood to processing bag.
3. Add HES to processing bag (20% v/v). (Optional)
4. Load processing bag set onto auto expresser.
5. Centrifuge at an uninterrupted Run at two different speeds: 1,400 G for 20 min. to segregate WBC at RBC/plasma interface and 85 G for 5 min. to express the RBC to the RBC bag and WBC to freezing bag.
6. Tube seal and separate excess RBC and plasma bags from processing set.
7. Add 5 ml cryoprotectant to WBC in freezing bag at 4° C.
8. Tube seal and separate freezing bag from cryoprotectant line.

Complete collection of the first component is indicated preferably by an optical sensor that is present in the bag set holder device. The servo motor, directed by the sensor, automatically closes the metering valve on the line, terminating collection of that particular component. The servo motor then further engages the metering valve to allow collection of the next component through a second output line connecting the metering valve and the second storage bag. The process may sequentially continue until all desired components are collected in separate storage bags: red blood cells, white blood cells (lymphocytes and granulocytes), platelets, and plasma. If so desired, multiple components, such as the white blood cells and the platelets can be directed to the same storage bag. The sensor may be other than optical. For example, the sensor may monitor changes in electrical characteristics inherent in differing densities, such as capacitance, viewing the fluid as a dielectric. Commercially available markers (e.g. monoclonal antibodies, polarized particles, magnetic density, or fluorescence markers, etc.) can be introduced into the blood and monitored.

The bags receiving fluid components may also be supported for weighing both during centrifugation and when at rest. Accurate separation occurs.

Once collected, each storage bag may be sealed off and separated from the whole blood processing bag. Any necessary preservatives or additives may be introduced through the collection lines before processing or storing.

OBJECTS OF THE INVENTION

Accordingly, it is a primary object of the present invention to provide a new and novel device and method for separating the components of whole blood for subsequent storage or use.

It is a further object of the present invention to provide a device and method as characterized above in which separation may be accomplished entirely by machine during a single uninterrupted centrifugation run without the considerable handling between multiple centrifugation runs typically practiced in a blood bank with conventional means of separating blood components.

A further object is to precisely sequester red blood cells, plasma, platelets and white blood cells even separating within white blood cell populations.

It is a further object of the present invention to provide a device and method as characterized above in which the separation apparatus is self-contained to simplify the operation.

Viewed from a first vantage point, it is an object of the present invention to provide a device for sequestering components from whole blood, comprising, in combination: a bag set, said bag set including a first bag and plural other bags; a bag set holder, whereupon the first bag is contained within an interior portion of the bag set holder, and the plural other bags are located at an elevation lower than said first bag; and a centrifuge having at least two diametrically opposed receiving sockets, at least one socket dimensioned to receive the bag set holder.

Viewed from a second vantage point, it is an object of the present invention to provide an apparatus for use with a conventional centrifuge and a blood processing bag set, comprising, in combination: a first pocket having an unenclosed top portion, the first pocket dimensioned to receive a blood processing bag; means to support the blood processing bag in the first pocket, the support means located adjacent the unenclosed top portion of the first pocket; a movable bottom portion below the first pocket, the movable bottom portion having an open position and a closed position; a hinged portion located along a long axis of the first pocket, the hinged portion opening to allow access to the first pocket when the movable bottom portion is in the open position; and a second pocket, wherein access to the second pocket is only possible when the movable bottom portion is in the open position.

Viewed from a third vantage point, it is an object of the present invention to provide a method for separating components from whole blood, the steps including: preparing a blood processing bag set having a processing bag, at least one auxiliary bag, a sampling site adjacent the processing bag, and a sampling site adjacent each auxiliary bag; introducing whole blood into the processing bag; sampling the whole blood for later analysis; centrifuging the whole blood, wherein components are separated in the processing bag; directing each component into the at least one auxiliary bag of the blood processing bag set; removing a sample of each component for later analysis; and storing each component for later use.

Viewed from a fourth vantage point, it is an object of the present invention to provide a bag set, comprising, in combination: a first bag having an inlet and an outlet; plural auxiliary bags, each auxiliary bag having at least one port for admitting or expelling contents of the auxiliary bags; conduit means leading from the first bag to each auxiliary bag; valve means on the conduit means, the valve means adjustable to allow selective access between the first bag and the plural auxiliary bags.

These and other objects will be made manifest when considering the following detailed specification when taken in conjunction with the appended drawing figures.

BRIEF DESCRIPTION OF THE DRAWINGS

FIG. 4 shows the bag set in position in the bag holder in open position.

FIG. 5 shows the bag set in position in the bag holder in closed position.

FIG. 6 shows positioning of two bag holders in a conventional centrifuge.

FIG. 12 is a flowchart of the preferred process.

FIG. 13 illustrates the separation of whole blood components in graphical form.

FIGS. 14A, 14B, 14C show the operating positions of the metering valve.

DESCRIPTION OF PREFERRED EMBODIMENTS

Figure 3:
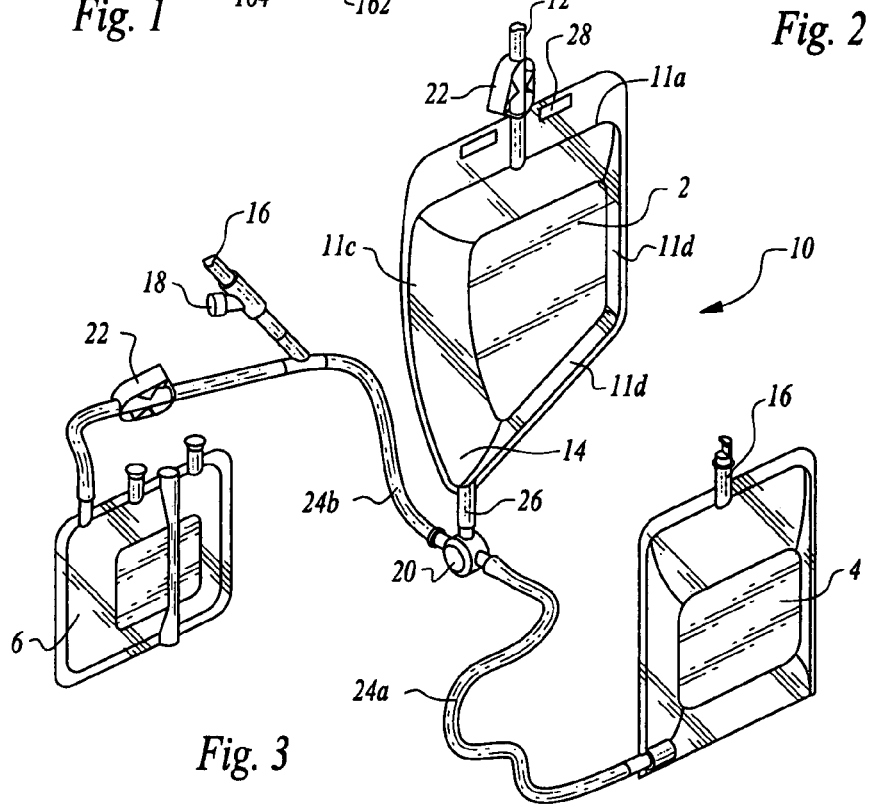
FIG. 3 shows the bag set of the present invention.

Considering the drawings, wherein like reference numerals denote like parts throughout the various drawing figures, reference numeral 10 as shown in FIG. 3 is directed to the bag set according to the present invention.

In its essence, the bag set 10 includes a whole blood processing bag 2, a red blood cell (RBC) bag 4 having a hanger 16, and a freezing bag 6 for the collection and storage of white blood cells. The processing bag 2 is supplied through an inlet line 12, either through a phlebotomy needle 8 (FIG. 10) or by being spiked, or sterile docked, to another bag containing the anti-coagulated blood. The processing bag 2 has an asymmetric shape including a top edge 11a, a short side edge 11b, a long side edge 11c, and a sloped bottom edge 11d between the side edges such that the bottom portion tapers to an asymmetric point 14, which leads to an outlet 26.

Asymmetric processing bag allows concentration of a monocular cell fraction of a white cell population in a time frame that excludes 30-50% of the granulocyte white cells. Granulocytes have no role in the hematopoietic reconstitution and, thus their deletion results in a more purified selection of white cells for transplant.

Also, the asymmetric bag set allows this purification to take place without the need for a sedimenting agent—which is too viscous to sterilize through a filter—thus allowing the MNC to be concentrated in a "closed" sterile bag set as the DMSO can be made sterile by passage through a 0.2μ filter at the cryoprotectant inlet to the bag set.

The outlet 26 directs output from the processing bag 2 into a three-way metering valve 20. The operating positions of the metering valve 20 are shown in FIGS. 14A-14C. Two supply lines 24a, 24b lead from the metering valve 20 to the RBC bag 4 and the freezing bag 6, respectively. The supply lines 24a, 24b and the inlet line 12 may each be heat sealed and separated from the bag set 10. All lines are equipped with line clamps 22 that may be closed to prevent fluid passage when desired. If other components are to be separated, the bag set 10 may include additional bags with a corresponding adjustment to the metering valve 20 to accommodate the additional bags.

Figure 10:
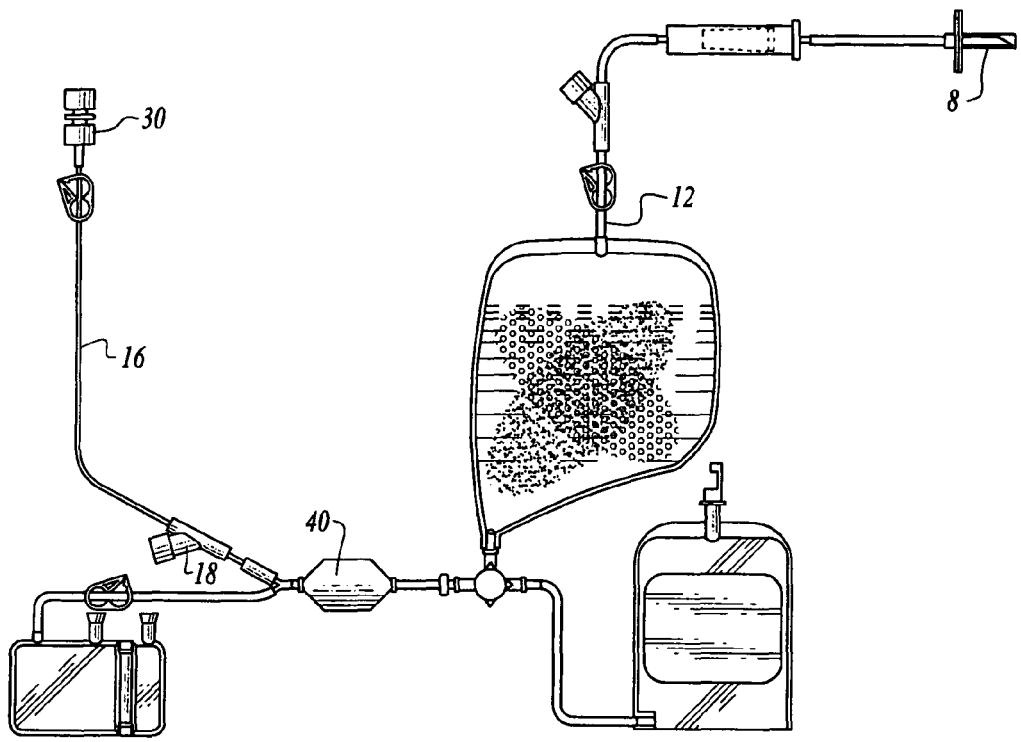
FIG. 10 shows the bag set after collection of a blood sample before components are separated.
Figure 11:
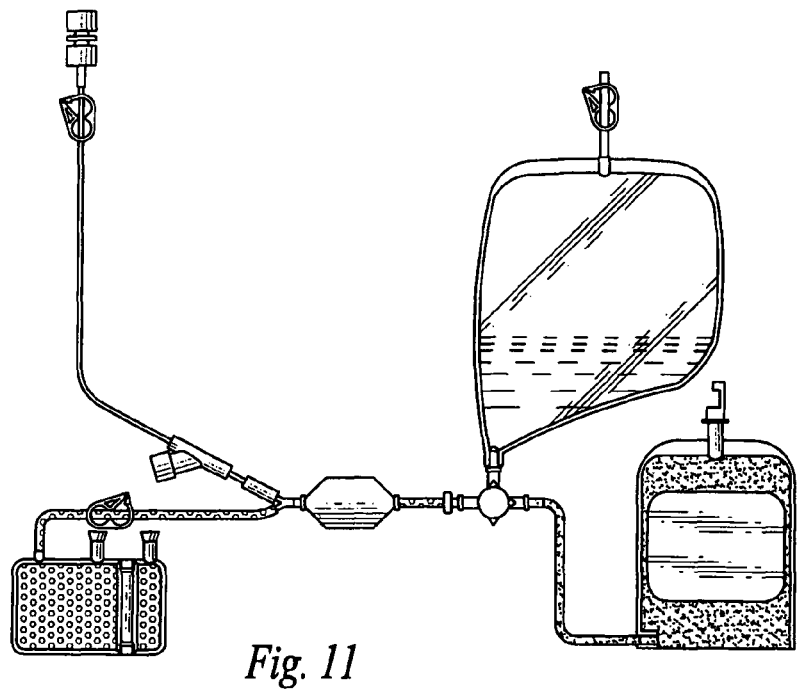
FIG. 11 shows the bag set after the red blood cell component is separated.
Figure 10A:
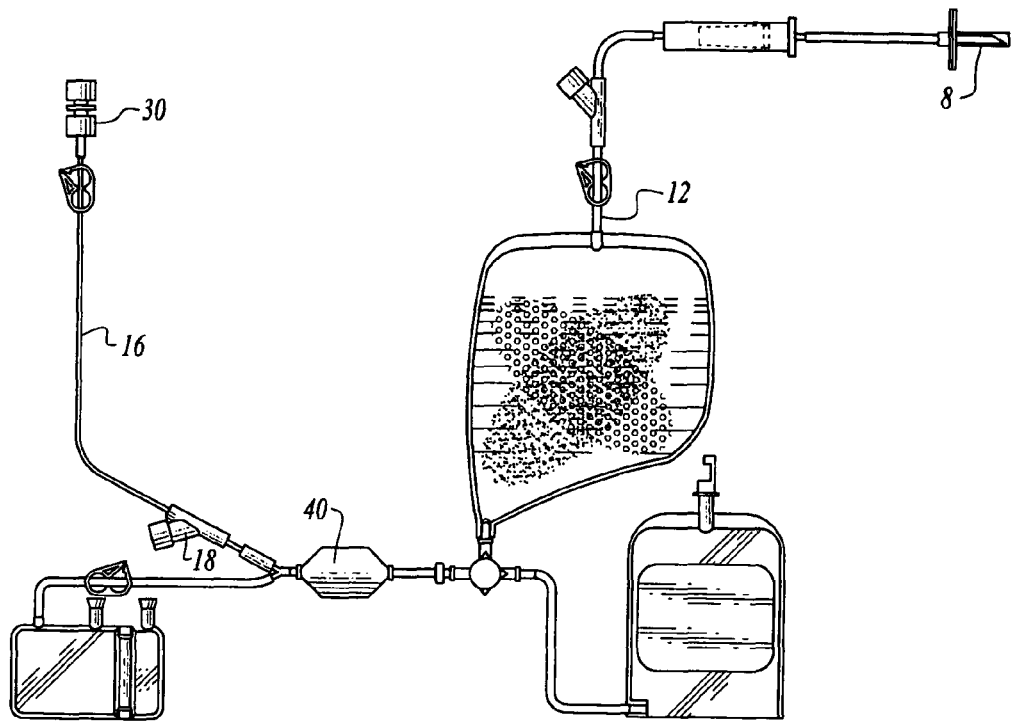
FIG. 10a depicts the same state as FIG. 10, but without the intermediate buffycoat bag.
Figure 11A:
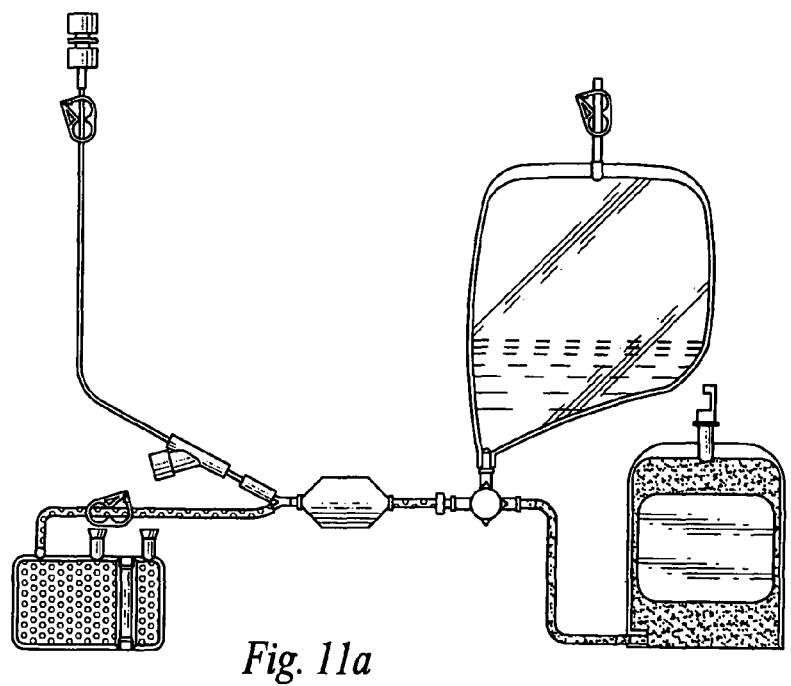
FIG. 11a depicts the same state as FIG. 10, but without the intermediate buffycoat bag.

Various supply lines may also be present in the bag set 10. For example, the freezing bag supply line 24b may have an inlet 16 for the introduction of cryoprotectant into the system. Such inlets may be equipped with filters 30 (see, e.g., FIG. 10), preferably 0.2μ filters, to, inter alia, prevent contamination from pathogens in the outside air and to allow venting of air from the freezing bag and tubing. An intermediate buffycoat bag 40 (FIG. 10) may be present on the freezing bag supply line 24b. The buffycoat bag 40 collects a separate white cell fraction, which includes platelets and white cells and includes some small volume of plasma or red blood cells. FIGS. 10a and 11a show the bag set without the intermediate buffycoat bag 40.

Figure 8A:
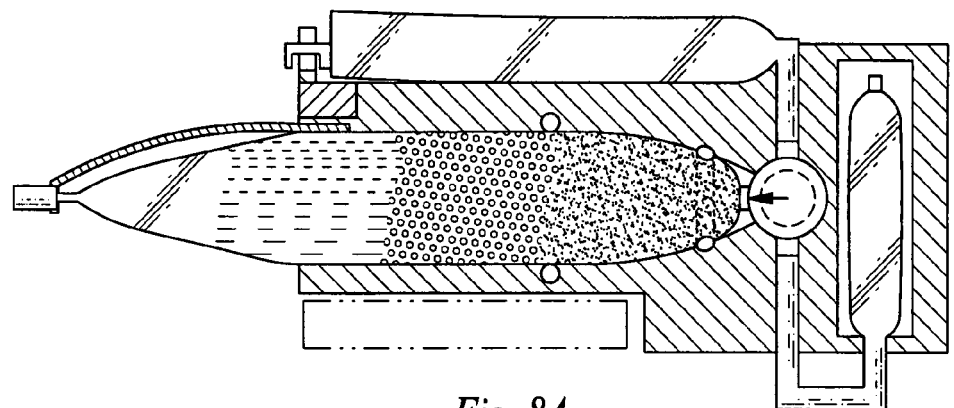
FIGS. 8A, 8B, 8C show the stages of harvesting components from the processing bag.

Initially, the processing bag 2 is either filled with an anti-coagulant, such as CPD (citrate, phosphate, and dextrose) and blood is drawn through a phlebotomy needle into the bag, or the inlet line is spiked or sterile docked to another bag containing anticoagulated blood. The metering valve 20 begins in the closed position (FIG. 8A). All clamps 22 are closed with the exception of the clamp 22 on the inlet line 12. Blood, preferably peripheral, placental umbilical cord blood, or bone marrow is obtained from a source through the phlebotomy needle 8 or other appropriate inlet, which feeds into the processing bag 2 through the inlet line 12. The inlet line 12 is then clamped, heat sealed, and separated from the bag set 10. Optionally, HES may be introduced into the RBC bag 4 through an optional inlet either before or after blood collection.

Figures 1, 2:
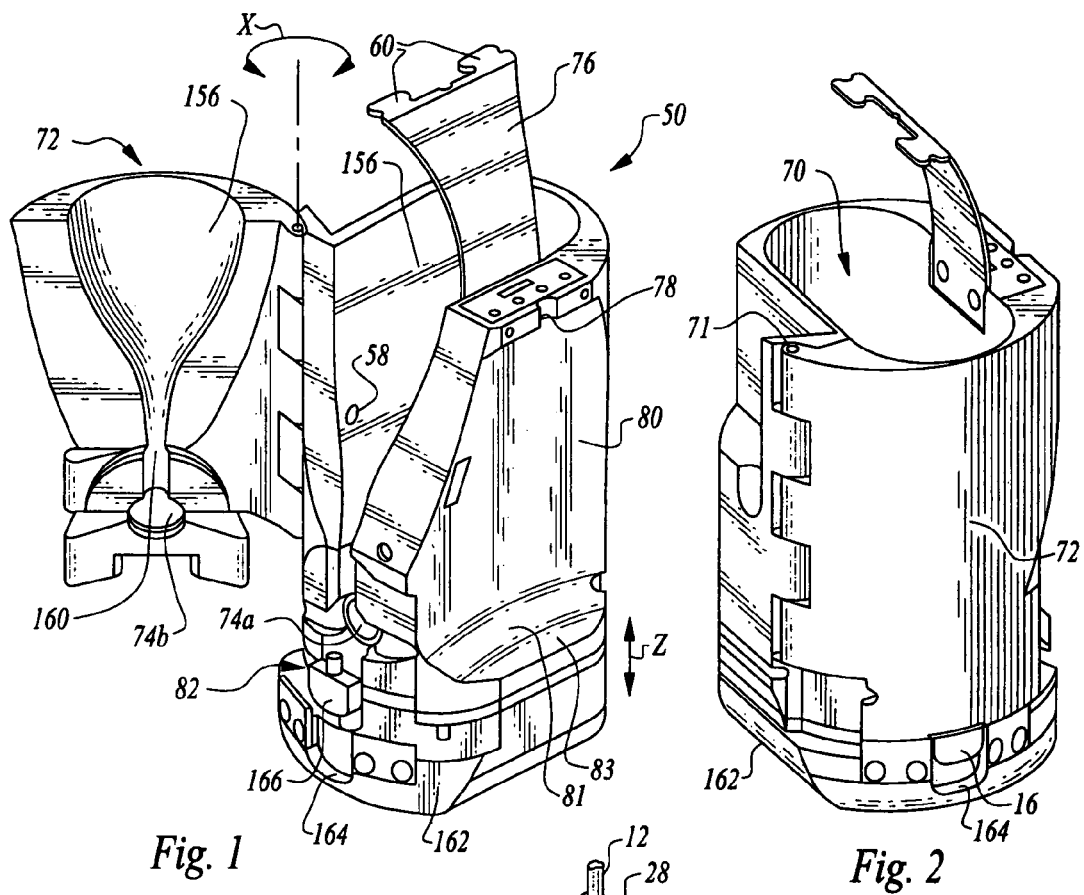
FIG. 1 shows the bag set holder of the present invention in open position.
FIG. 2 shows the bag set holder of the present invention in closed position

At this point, the bag set 10 is placed in a bag holder 50, shown in FIGS. 1, 2. The bag holder 50 is somewhat cylindrical, having a substantially elliptical shape, having two rounded ends connected by substantially straight sides. The main compartment 70 has an elongated oval shape dimensioned to receive the processing bag 2. The main compartment 70 is accessed by sliding down a bottom portion 162 of the bag holder 50 (along arrow Z), then opening a cover 72 about a hinge 71 (along arrow X) present at one of the rounded ends of the bag holder 50. The processing bag 2 is oriented in the bag holder 50 such that the hinged cover 72 closes over the edge 11c coinciding with the point 14 leading to the metering valve 20. The metering valve 20 is received in an orifice 74a located on the major portion of the bag holder 50. A complimental orifice 74b, located on the hinged cover 72, receives the protruding end of the metering valve 20. The hinged cover 72 will only close when the bottom portion 162 is in the closed position. When the bottom portion is closed, a notch 164 in the bottom portion 162 registers with a retaining tab 166 present on the main body of the bag holder 50.

Referring to FIG. 1, the bag holder 50 includes a bag hanger 76 having hooks 60 that engage the loops 28 on the processing bag 2, maintaining the bag in position during the centrifuging process. The main compartment 70 of the bag holder 50 is shaped to receive the processing bag 2, having a sidewall 156 that is complemental to the asymmetric shape of the processing bag 2, which terminates in an outport 160 dimensioned to receive the asymmetric point 14 and the outlet 26 of the processing bag 2. The sidewalls 156 cradle the processing bag 2 loosely around the middle and more tightly at the bottom (near the outlet 26). Closer tolerance near the bottom of bag 2 is desired to minimize disturbing the contents of the bag after sedimentation. Thus, the top of compartment 70 mirrors the exterior elliptical shape but tapers down to the outport 160 while maintaining bag edges 11b,11c,11d in supporting relationship.

Figure 37:
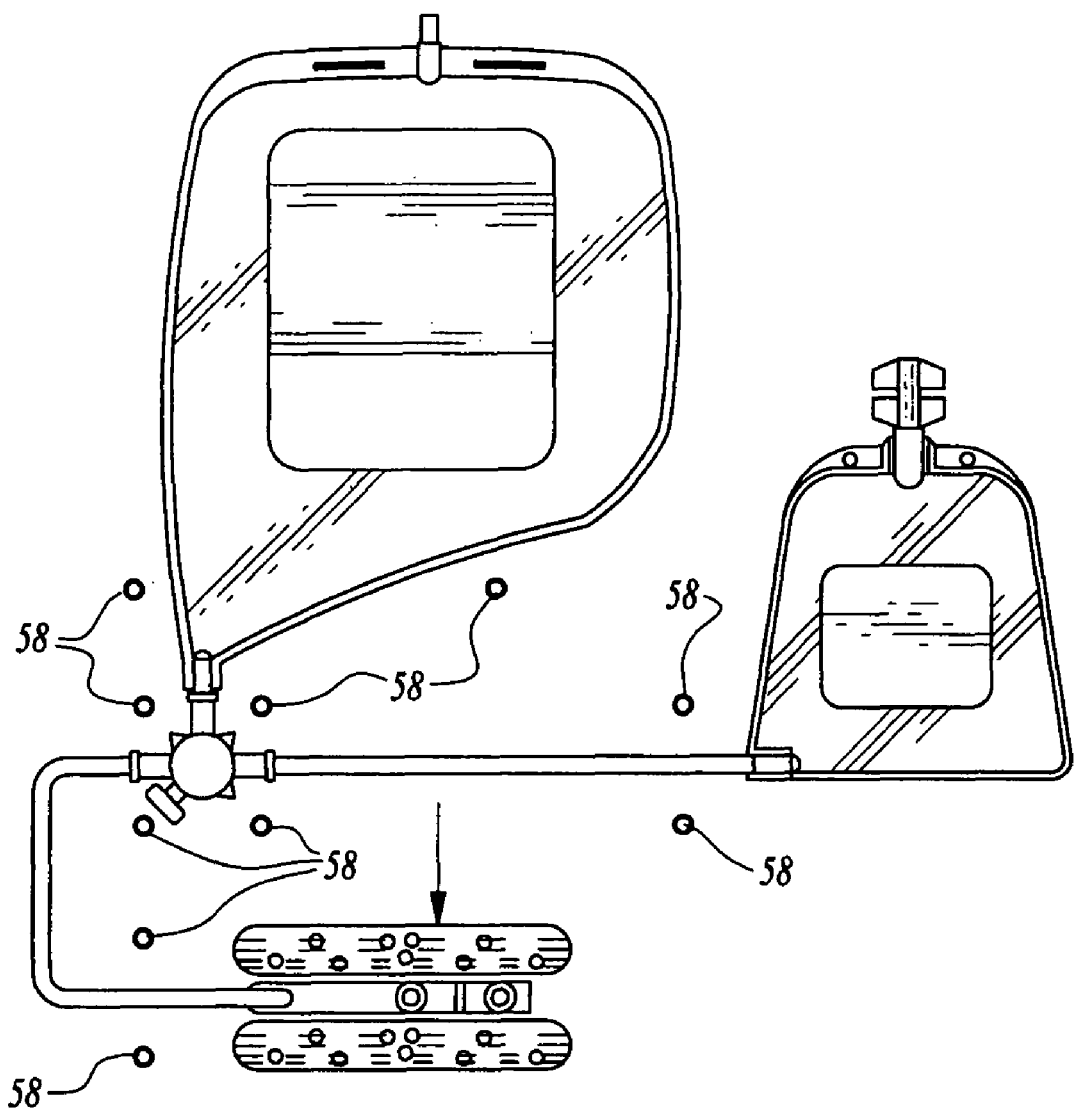
FIG. 37 is a further iteration of a bag set schematically showing freezer bag (white blood cell) weighing during centrifugation.
Figure 38:
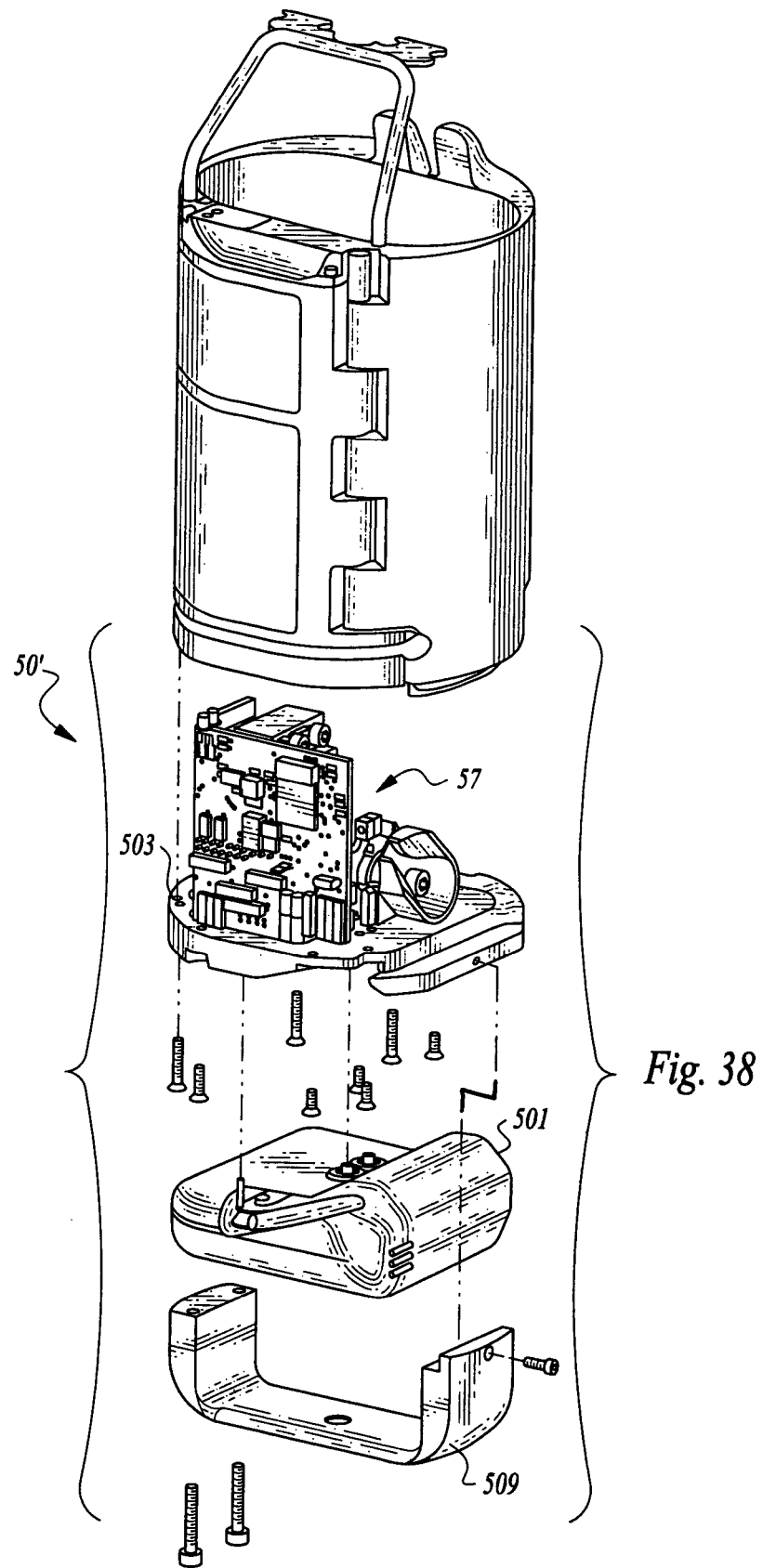
FIG. 38 reflects an alternate processing device 50.
Figure 39:
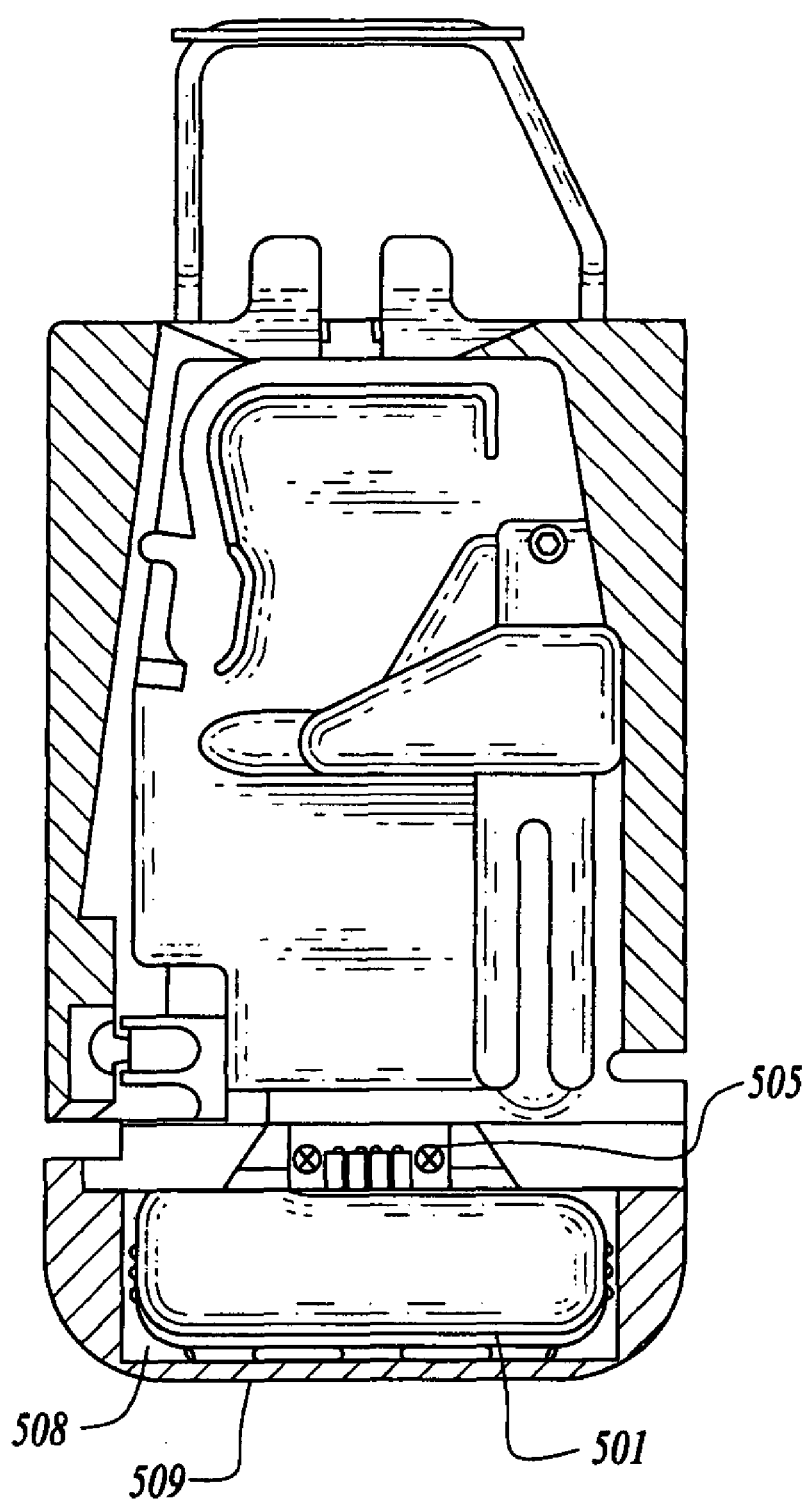
FIG. 39 is another view of FIG. 38.

A notch 78 is present along one of the substantially straight sides of the bag holder 50. The notch 78 receives the hanger 16 on the RBC bag 4. The RBC bag 4 hangs along the outside of the bag holder 50 in a curved recess 80 leading to a lower support shelf 83 via transition 81. The freezing bag 6 is cradled in a receptacle 82 located beneath the main compartment 70 of the bag holder 50, accessed by sliding the bottom portion 162 down to open along arrow Z. FIGS. 4 and 5 show the entire bag set 10 loaded in the bag set holder 50 before component separation occurs. FIG. 37 shows a further iteration of a bag set showing schematically that the freezer bag is weighed during the separation process. FIG. 38 shows the freezer bag has been encapsulated in a shell 501 which depends from platform 503 that supports, on its top side a control chip module 57 and on its bottom side the shell and freezer bag via a weighing load cell 505. Shell 501 floats in an air space 508, protected by "U" shaped bracket 509.

Figure 35:
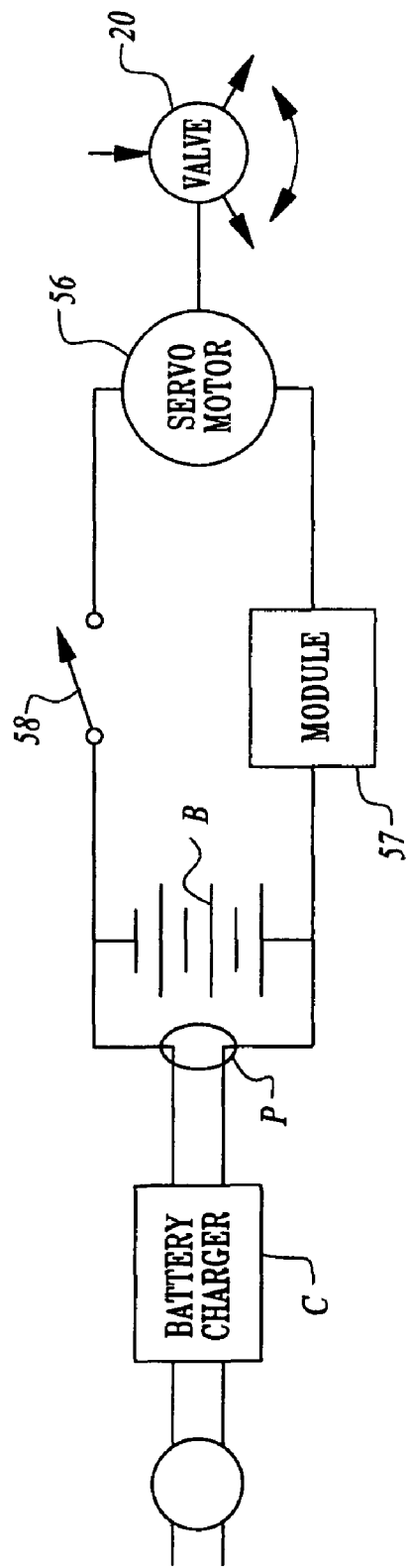
FIG. 35 is a schematic of the servo motor and valve system connections.

The metering valve 20 is connected to a motor driver 56 in the bag holder 50. The servo motor 56 is connected to a software-controlled control chip module 57 powered by a rechargeable battery B. Module 57 may require temperature compensation due to heat generation during centrifugation. A port P is provided to utilize a battery charger C (FIG. 35). The servo motor 56 controls the operation of the metering valve 20 while the bag set 10 is mounted in the bag holder 50. One or more optical sensors 58 trigger the proper time for the servo motor 56 to close the metering valve 20 after each fraction is harvested. The sensor may be present at the position shown in FIG. 1 or lower, closer to the outport 160 (FIG. 8C) adjacent the asymmetric point 14 of the processing bag 2. Sensors 58, for example may monitor all branches around valve 20 and the inlets of bags 4 and 6. The sensor 58 shown is optical but can be based on density, weight, infrared, radioactivity, fluorescence, color, magnetism, ultrasonics, capacitance, wherein the characteristic measured may be an additive.

Figure 8B:
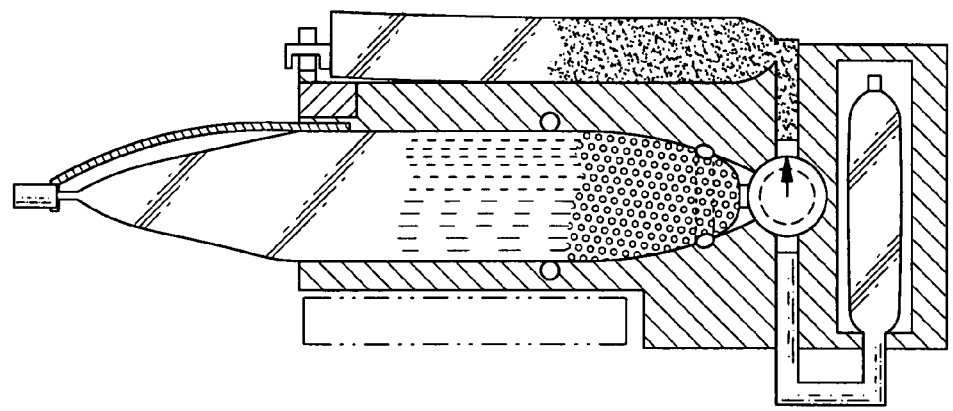
Figure 8C:
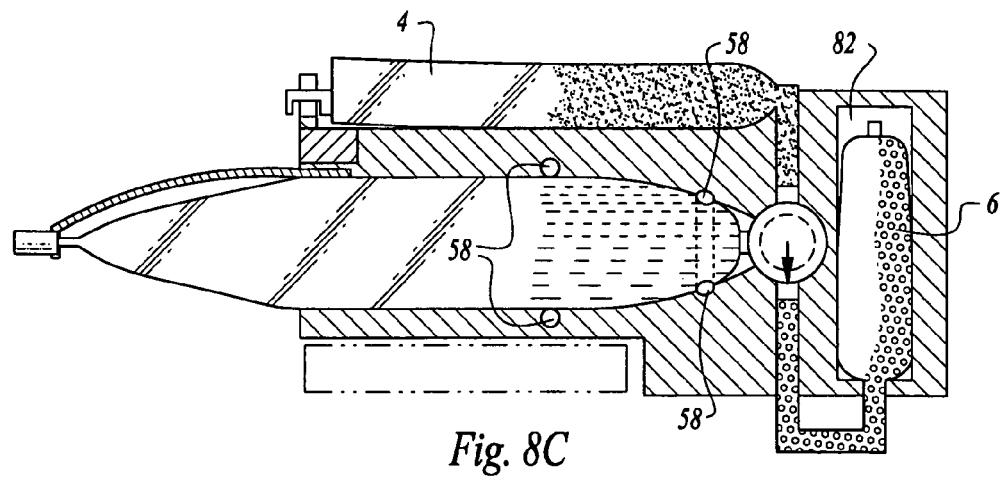

The bag holder 50, when closed, is adapted to fit into a centrifuge cup 66 dimensioned to reside within a conventional centrifuge 100. Preferably, at least two bag set holders 50 are placed in diametrically opposed centrifuge cups 66, as shown in FIG. 6, for balance. A bag set 10 in the centrifuge cup 66 may be subjected to more than one G-force in order to achieve the optimum stratification of components (FIGS. 8A-8C). The servo motor 56 then operates the metering valve 20 to open and allow access to supply line 24a for the harvest of red blood cells, at an optimum G-force, into bag 4. The servo motor 56 closes the metering valve 20 when the optical sensor 58 indicates that the red blood cells are harvested (FIGS. 8A, 8B). The optical sensor 58 senses the boundary between the white cell fraction and the plasma fraction.

Figure 9:
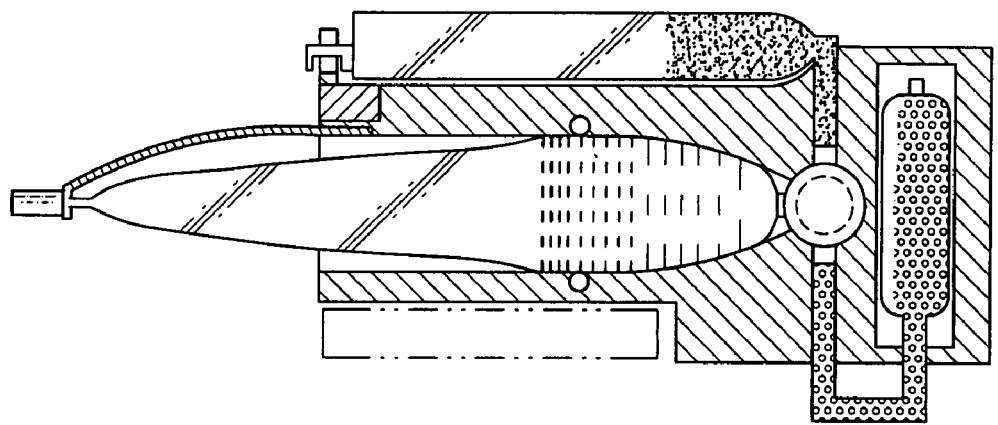
FIG. 9 shows the bag set in the bag set holder after component separation.
Figure 7:
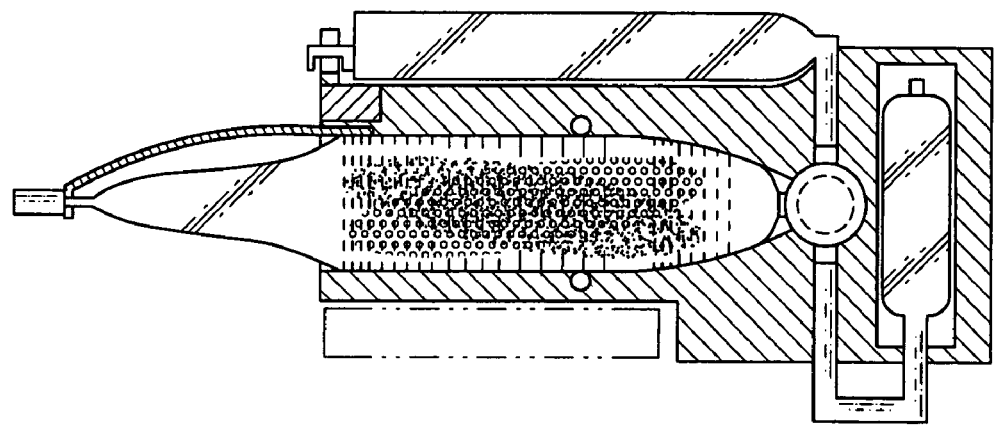
FIG. 7 shows the bag set in the bag set holder before component separation.

The next fraction, which includes white cells and/or platelets, is then harvested from the processing bag 2; the servo motor 56 opens the metering valve 20 to allow access to supply line 24b (FIG. 8C) leading to bag 6 for the next harvest. As shown in FIG. 9, during the harvest (WBC) into the freezing bag 6, air in the supply line adds to air already in the freezing bag 6, producing an air bubble 70, which is useful to assist the proper mixing of the WBC and/or platelets with the cryoprotectant. The servo motor 56 then closes the metering valve 20, as shown in FIG. 8A, and the centrifuge 100 is allowed to stop. FIG. 9 shows the bag set 10 in the bag set holder 50 after component separation has taken place.

The buffycoat bag 40, if present, preferably has a 25 ml capacity. 20 ml of buffycoat is introduced into the buffycoat bag 40, and 5 ml of DMSO solution is subsequently introduced. The buffycoat bag is placed between two cold strata and rotating or kneading of the buffycoat bag 40 in order to mix the cryoprotectant and WBC solution takes place.

The bag holder 50 is removed from the centrifuge cup 66 and opened, and the bag set 10 is removed, with the servo motor 56 disconnected from the metering valve 20. Each supply line 24a,24b is clamped, heat sealed, and removed from the processing bag 2. Any additional bags may be similarly removed.

After the supply line 24b connected to the freezing bag 6 is disconnected, a cryoprotectant may be introduced into the collected component in the freezing bag 6 through an inlet. The air bubble 70 in the freezing bag 6 allows the cryoprotectant to be thoroughly mixed with the collected component. After mixing, the air bubble 70 is expelled, perhaps through a filter-protected cryoprotectant inlet 16 (FIG. 10). The component is then prepared for storage by heat-sealing the tubing and removing the bag 6 downstream of the cryoprotectant inlet 16.

Preferably, each line (the inlet line 12 and the supply lines 24a,24b) is oriented to allow access to a sampling site (e.g., site 18) near the collection or storage bags. Thus, a sample of the blood or fluid in the line may be taken without disturbing the bulk of the collected component.

FIG. 13 depicts the separation of whole blood components as a function of time. Under centrifugation, each fraction stratifies in the processing bag 2 as a function of its density. The overlapping areas 175 (FIG. 13) indicate the area in the separation along each strata line in the processing bag 2. As centrifugation continues, the boundary of each fraction becomes more clearly defined; thus, the area 175 (FIG. 13) decreases and each fraction is more completely harvested. Thus, the centrifugation strategy combines separation by density, the time involved for stratification, which differs with the exterior surface area and density of the various cells, centrifugal force, and boundary layer clarity. Decisions on harvesting will vary based on these tradeoffs as a function of the constituent of greatest value and its desired purity.

Figure 36:
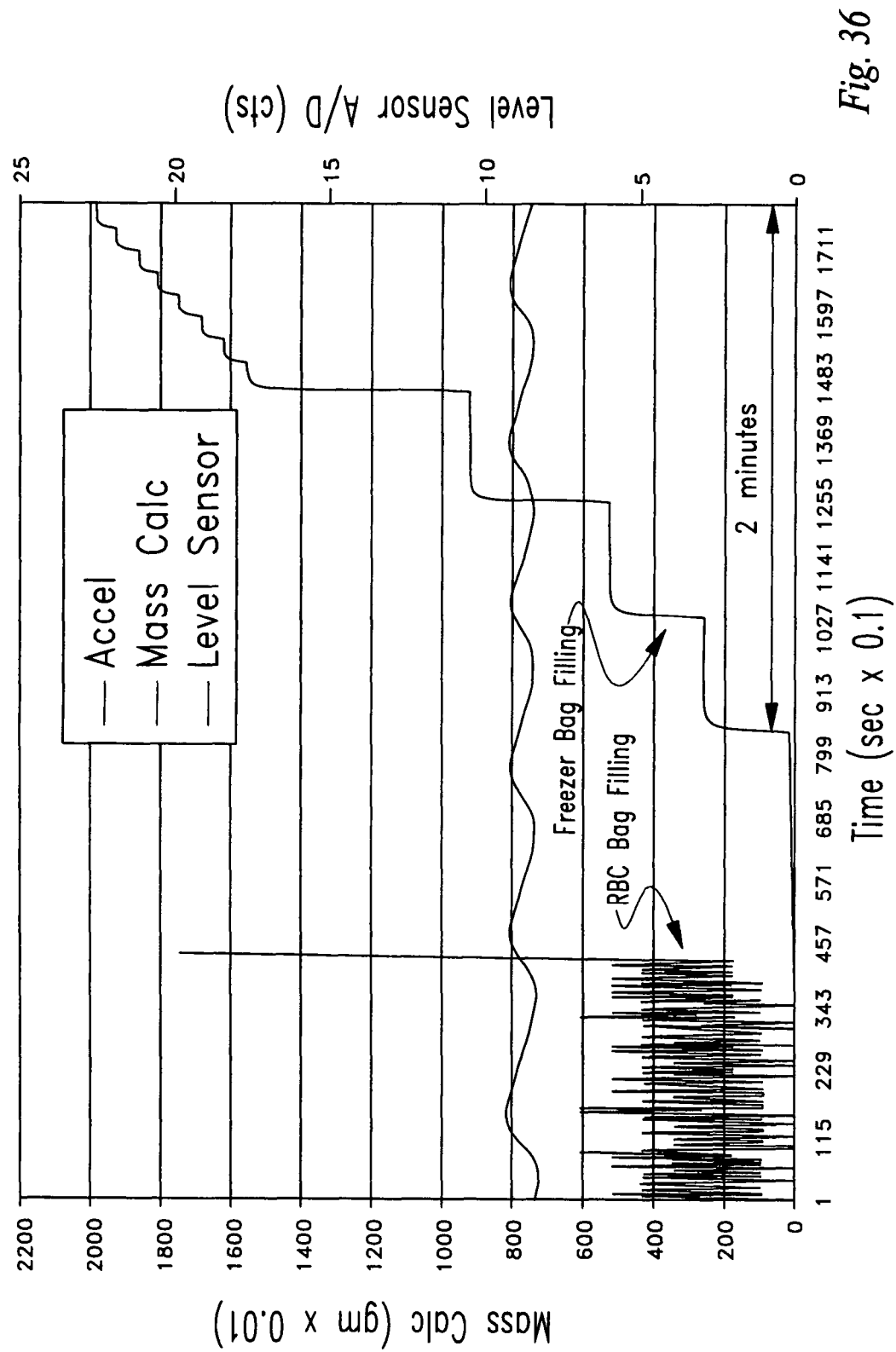
FIG. 36 plots, as a function of time while centrifuging: mass and liquid levels monitored by sensors. Also shown is the series of on/off valve rotations causing incremental weight increases of the harvested WBC solution, resulting in a full WBC freezing bag.

Preferably, the stratification centrifugation occurs at an excess of 1000 Gs, preferably 1400 Gs, for approximately 20 minutes. The transfer centrifugation step occurs at less than 100 Gs, preferably 78 Gs, and stops subject to output from the optical sensor 58. The right hand side of FIG. 36 shows the white cell bag (Freezer bag 6) topped off in increments by throttling the valve 20 on and off in order to extract the WBC population.

It is appreciated that while the instant invention is preferably used in the separation of blood components, the separation techniques and apparatus are suitable for separation of other fluids. The software programmed into the control chip module may cause the servo motor to open and close the valve many times, thereby throttling the valve during strata delivery. Also by varying time increments during a harvest procedure, precise cut-offs between the cell components can be achieved in order to reduce the mixing between cell types that may occur as a result of the "toroidal" (Coriolis) effect during removal of the blood component from processing bag 2 and may be modified for the separation of other fluids or to compensate for various hardware conditions, such as uneven centrifuge loading.

Figure 15:
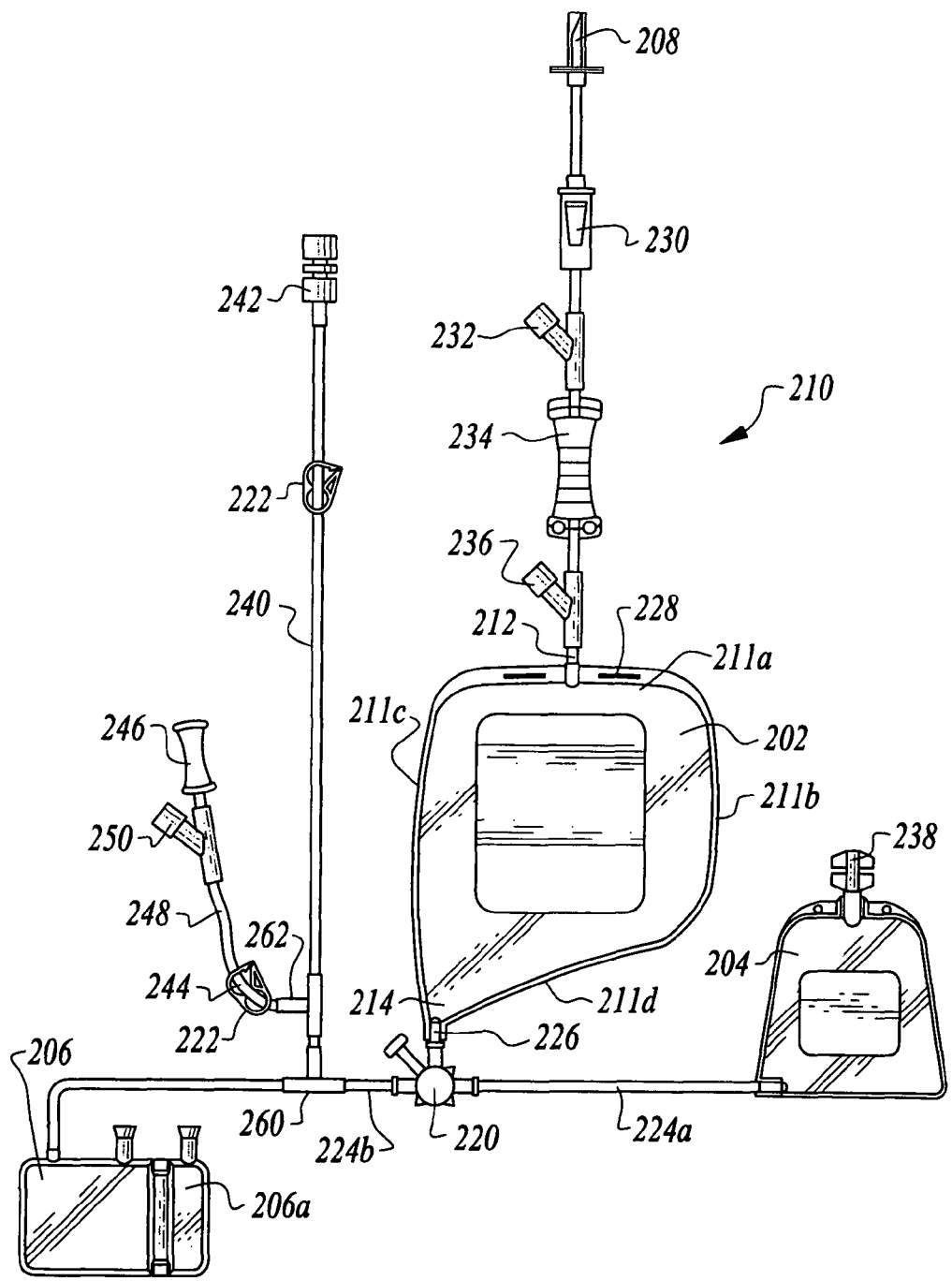
FIG. 15 shows an alternative embodiment of the bag set.

Yet another embodiment of the bag set 210 is shown in FIG. 15. In its essence, the bag set 210 includes a whole blood processing bag 202, a red blood cell (RBC) bag 204, and a freezing bag 206. The processing bag 202 is supplied through an inlet line 212 that terminates in a spike 208. The processing bag 202 has an asymmetric shape including a top edge 211a, a short side edge 211b, a long side edge 211c, and a sloped bottom edge 211d between the side edges such that the bottom portion tapers to an asymmetric point 214, which leads to an outlet 226. The outlet 226 directs output from the processing bag 202 into a stopcock valve 220. Two supply lines 224a,224b lead from the stopcock valve 220 to the RBC bag 204 and the freezing bag 206, respectively. The supply lines 224a,224b and the inlet line 212 may each be heat sealed and separated from the bag set 210. All lines are equipped with line clamps 222 that may be closed to prevent fluid passage when desired. If other components are to be separated, the bag set 210 may include additional bags with a corresponding adjustment to the stopcock valve 220 to accommodate the additional bags.

Figure 16:
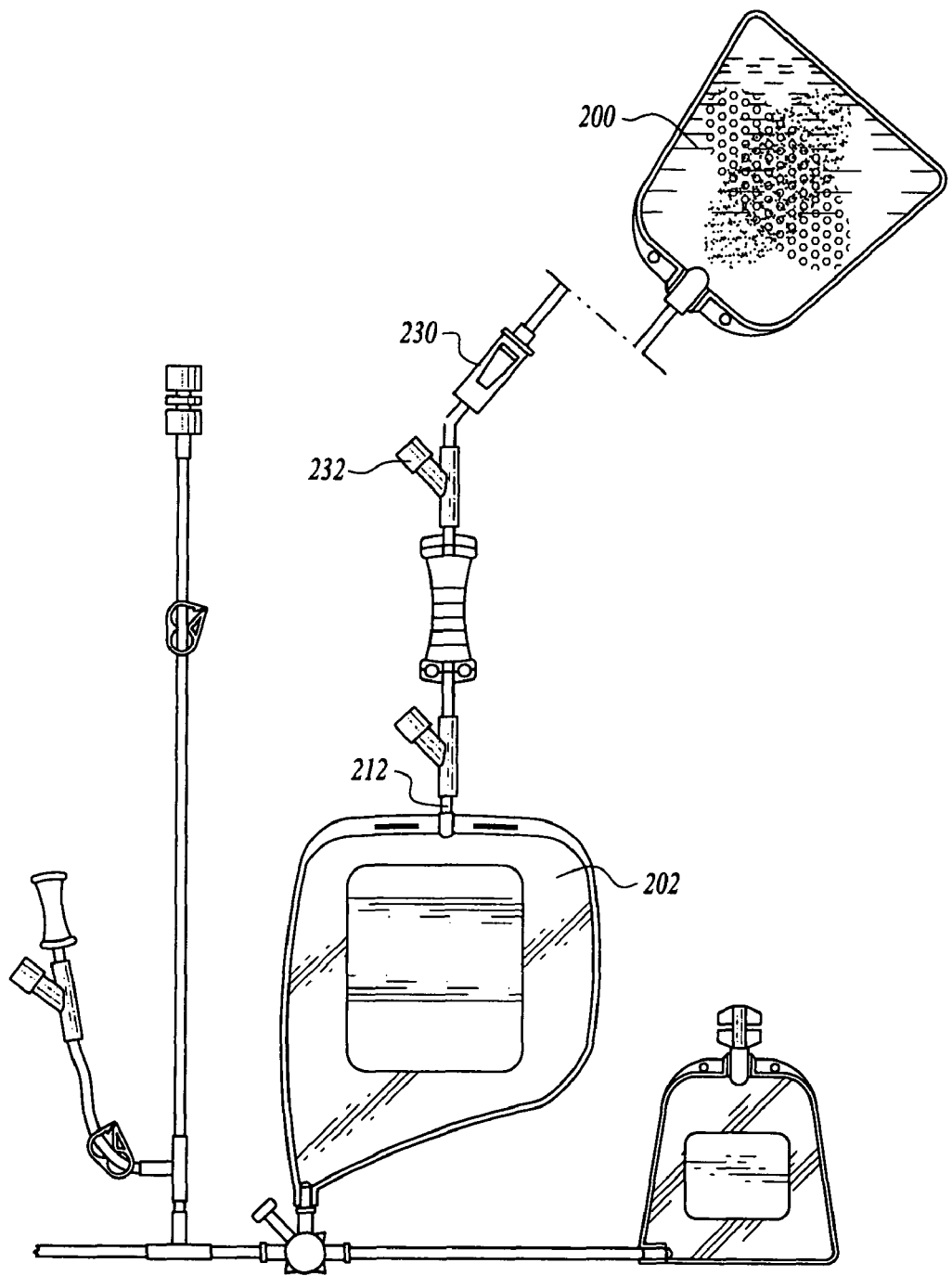
FIG. 16 shows the attachment of a collection bag to the bag set.
Figure 17:
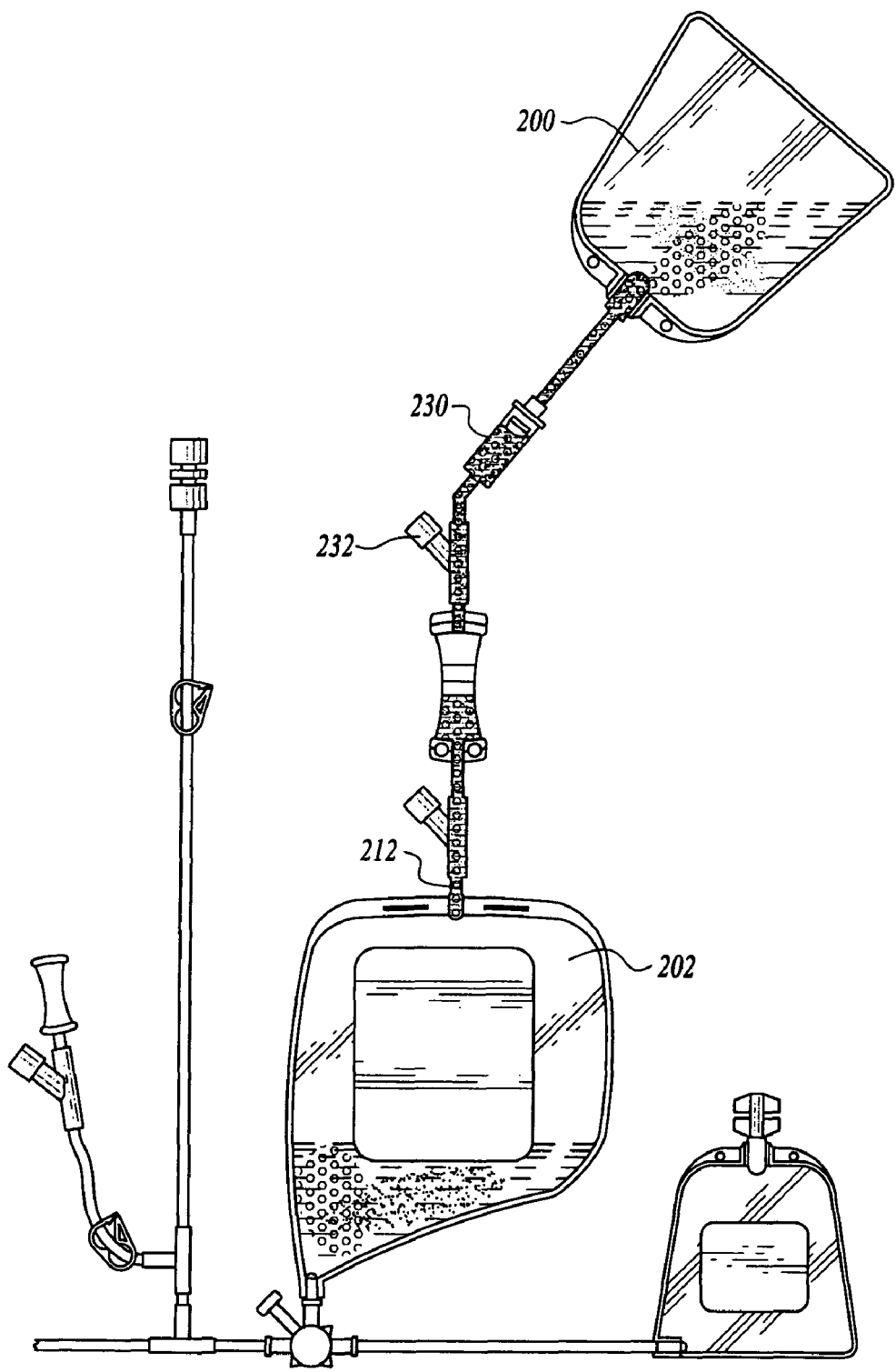
FIG. 17 shows the operation of draining the contents of the collection bag into the processing bag of the bag set.
Figure 18:
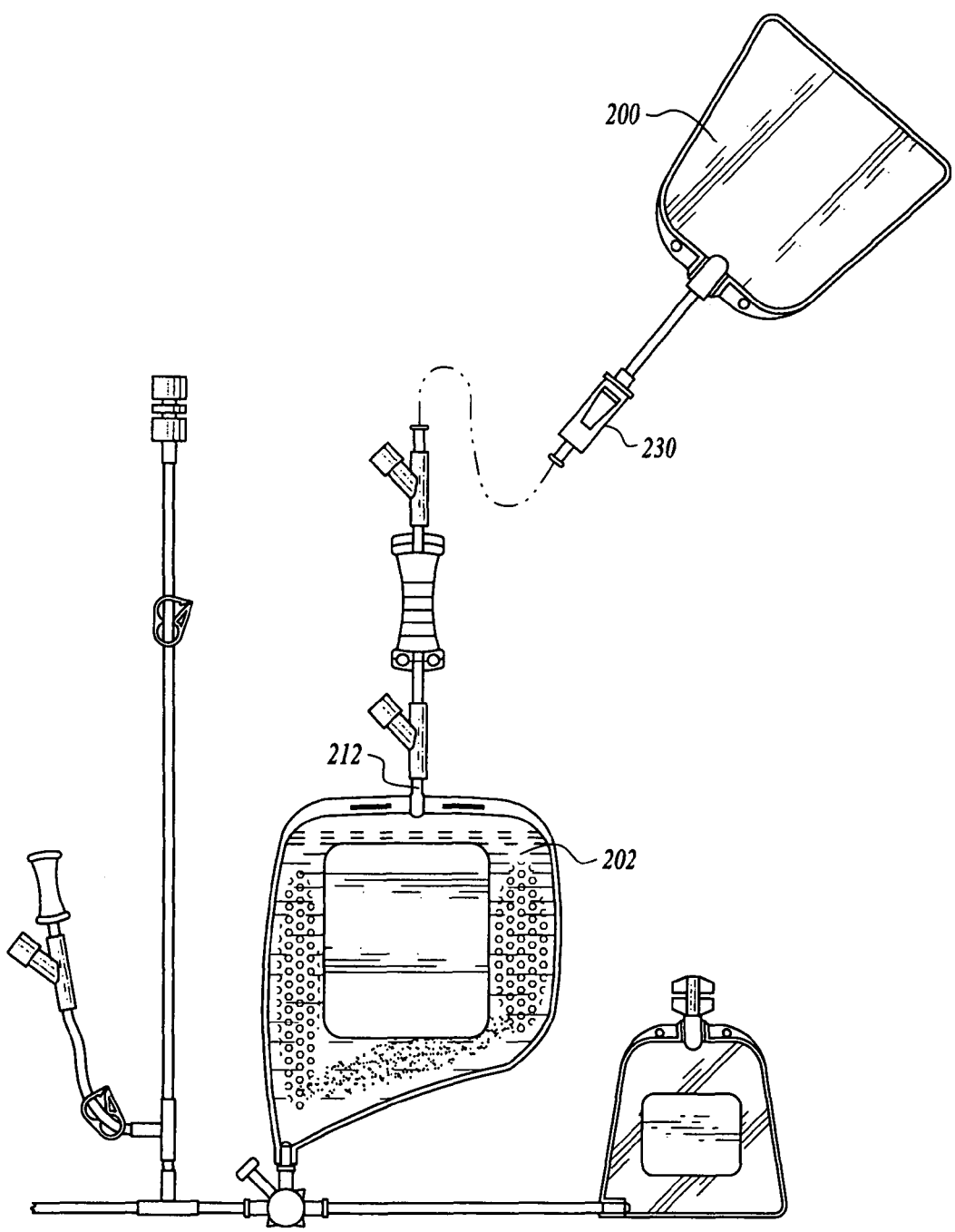
FIG. 18 shows the disconnection of the connection bag and clot filter from the bag set.

Initially, the blood of interest is collected in a collection bag 200 or similar container. The spike 208 is inserted into the collection bag 200, and the blood is drained from the collection bag 200 into the processing bag 202 through the inlet line 212 (FIGS. 16, 17). The inlet line 212 preferably has a clot filter 230, through which the blood passes before it reaches the processing bag 202. After the blood is transferred, the inlet line 212 is heat sealed and the collection bag 200 and clot filter 230 are removed (FIG. 18).

Figure 19:
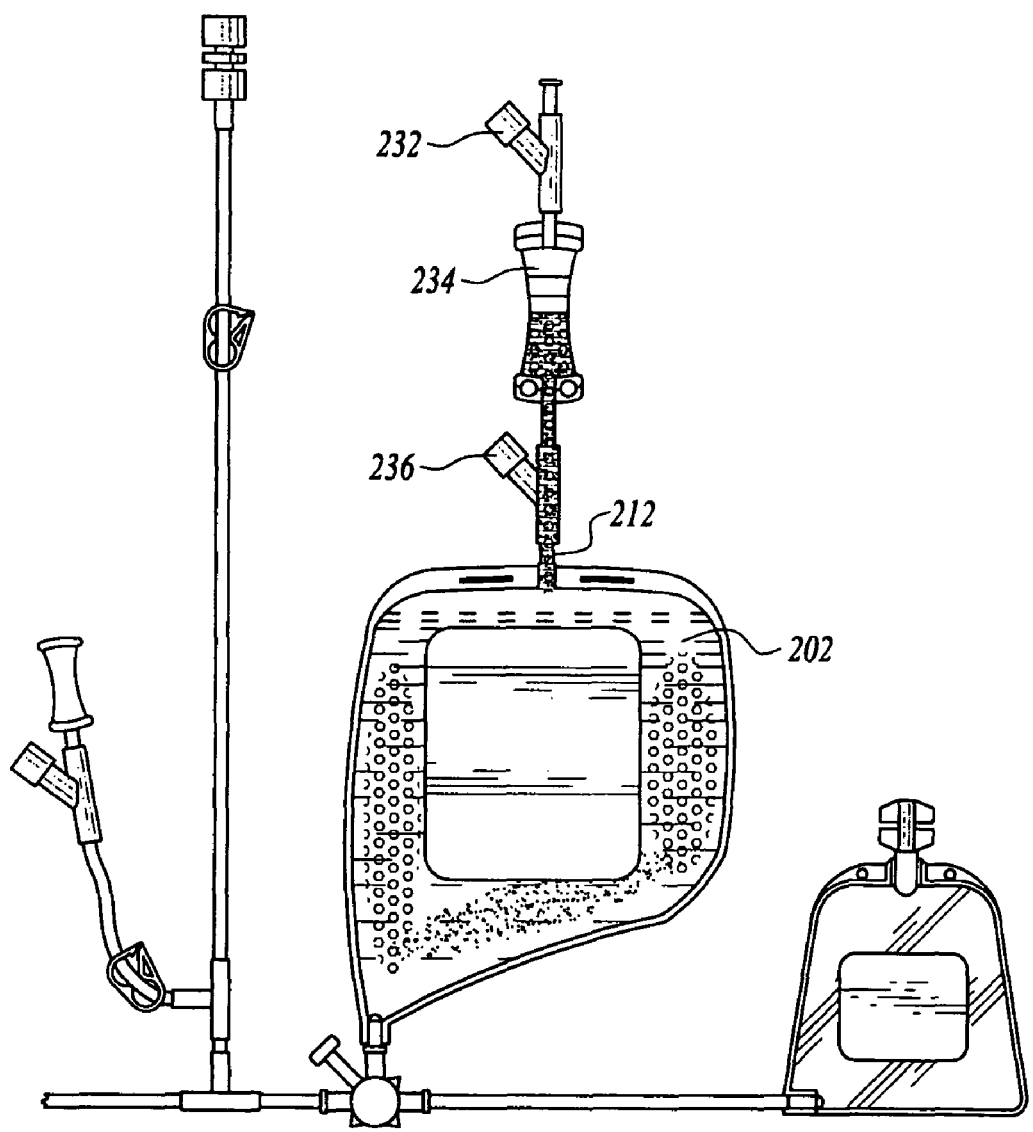
FIG. 19 depicts the process of filling the sampling pillow with blood from the processing bag.
Figure 20:
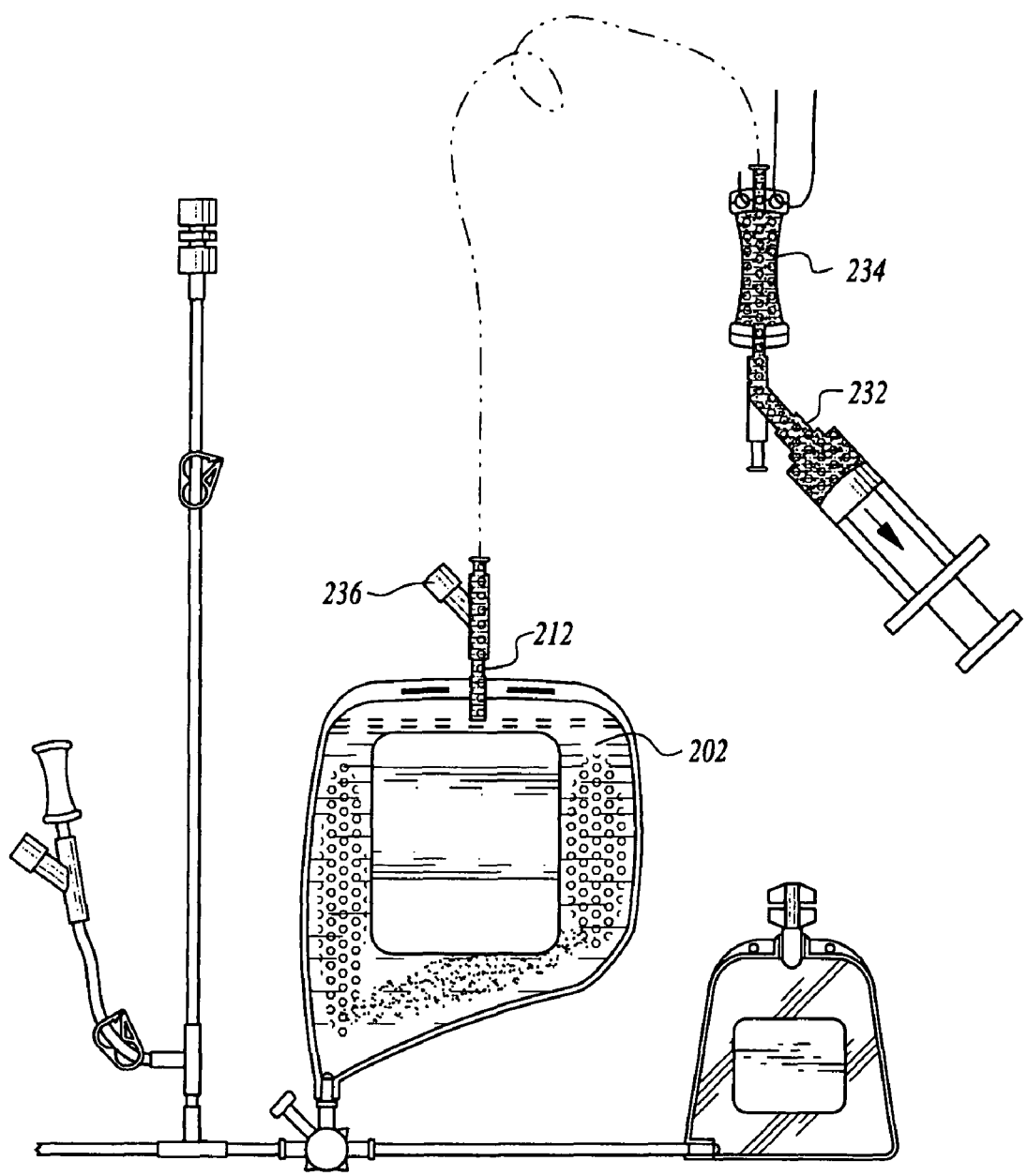
FIG. 20 shows the disconnection of the sampling pillow and its associated sampling port from the bag set.

The inlet line 212 also preferably has a sampling port 232, a sampling pillow 234, and an access port 236 (FIG. 19). After the collection bag 200 and clot filter 230 are moved from the inlet line 212, the sampling pillow 234 is squeezed and released to fill the sampling pillow with blood. The inlet line 212 is then heat sealed and the sampling pillow 234 is removed, along with the sampling port 232 (FIG. 20). The blood in the sampling pillow 234 may then be accessed through the sampling port 232 for separate assay.

Figure 21:
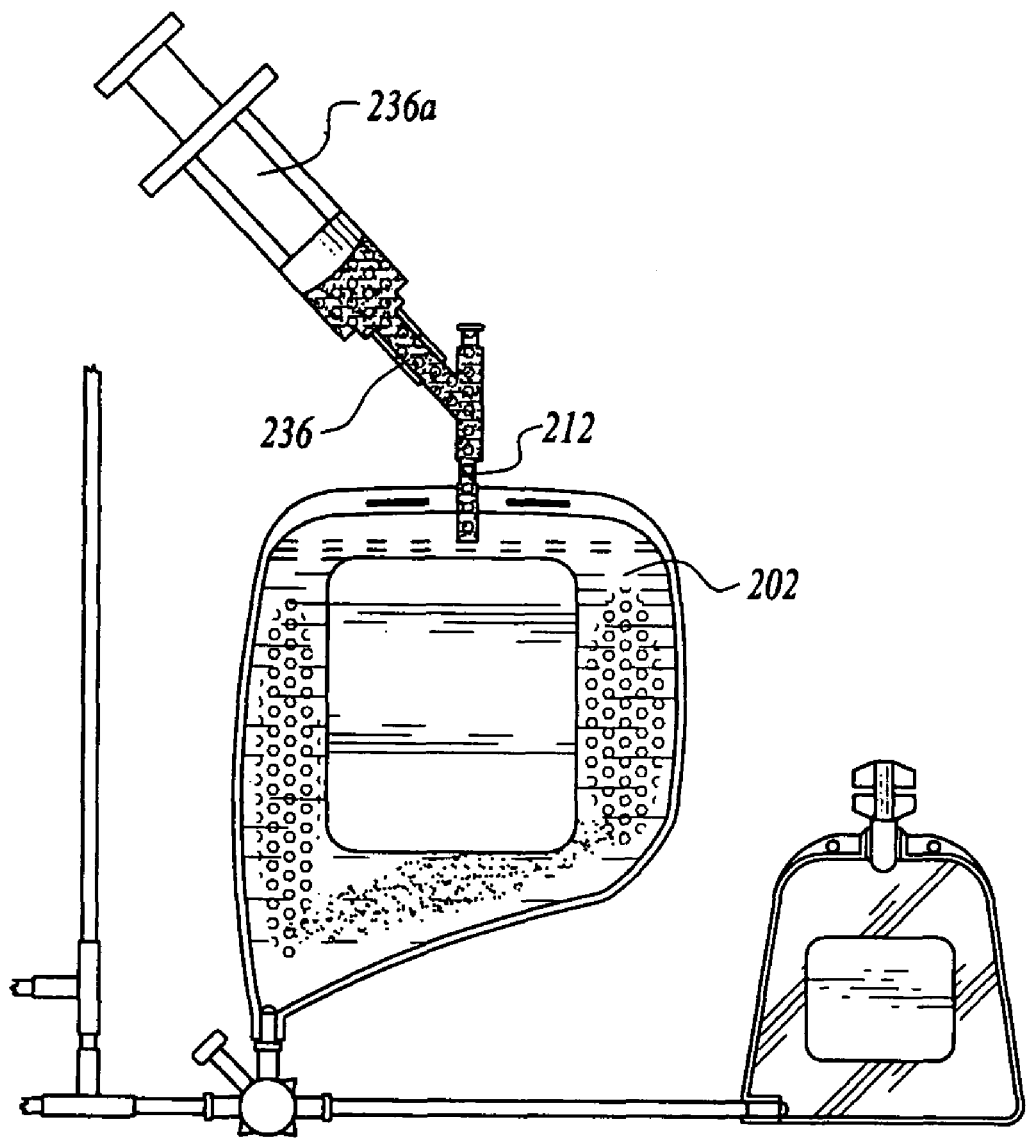
FIG. 21 depicts the addition of an optional sedimenting agent to the processing bag.
Figure 22:
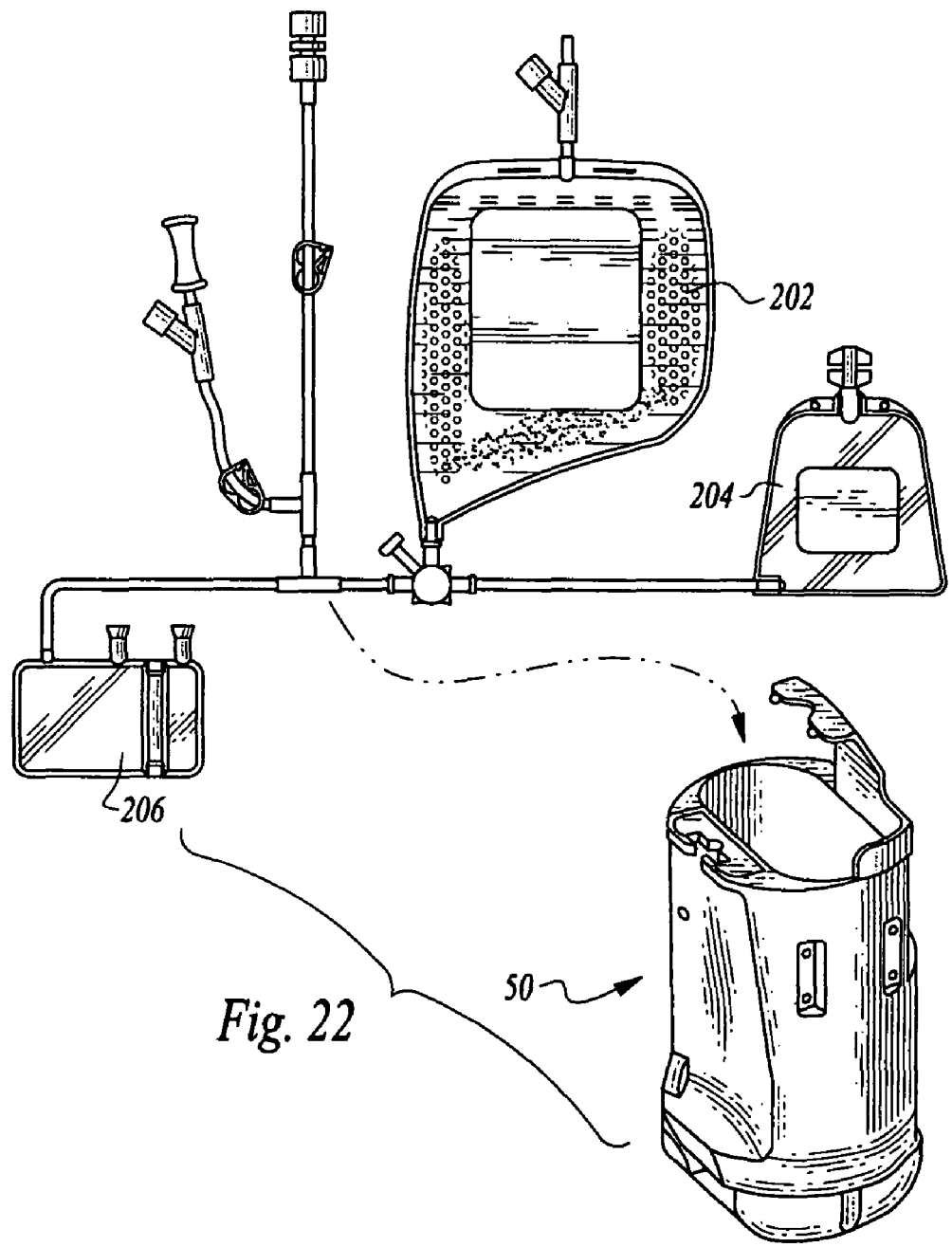
FIG. 22 illustrates the insertion of the bag set into the bag set holder.
Figure 23:
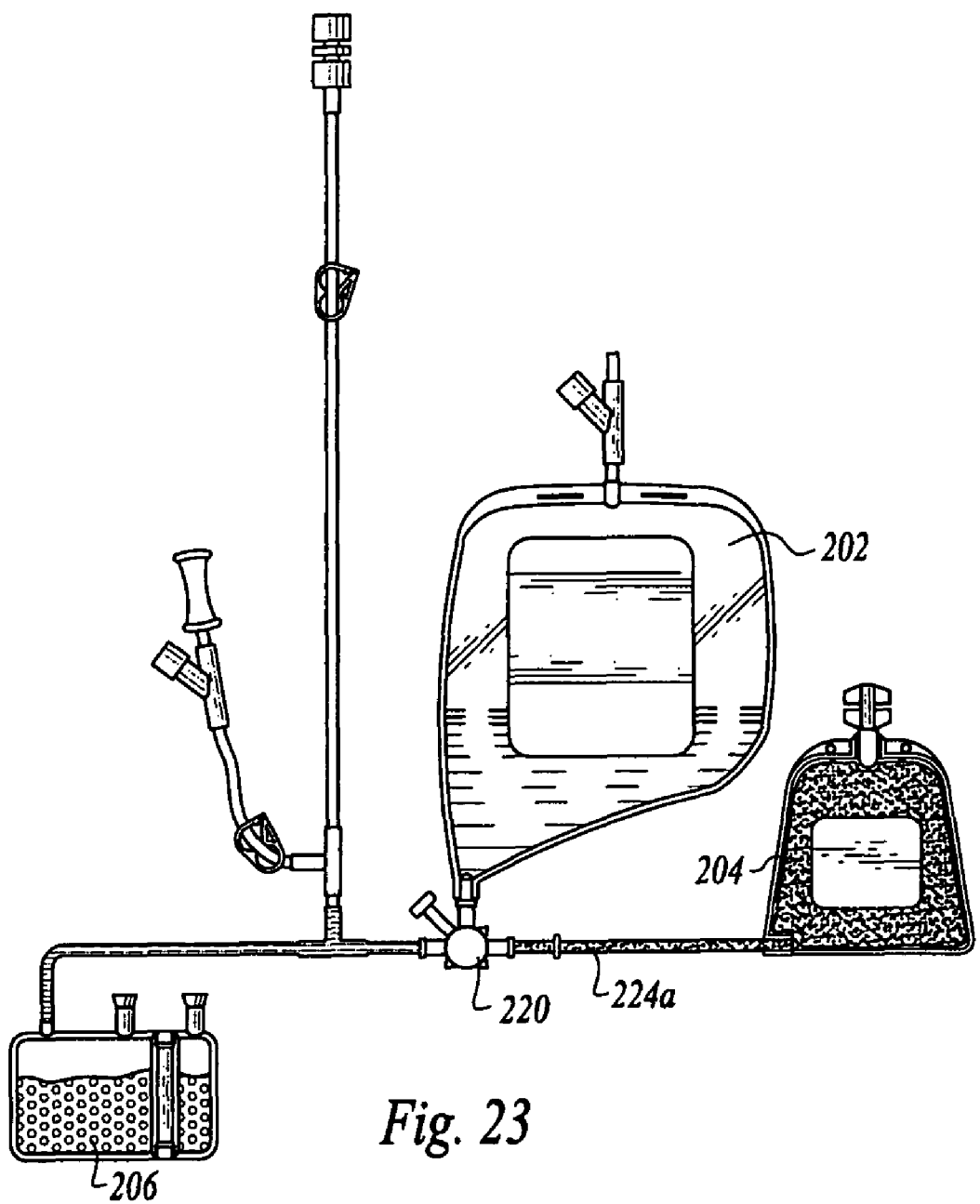
FIG. 23 is a depiction of the transfer of blood components that occurs under centrifuge while the bag set is in the bag set holder.
Figure 24:
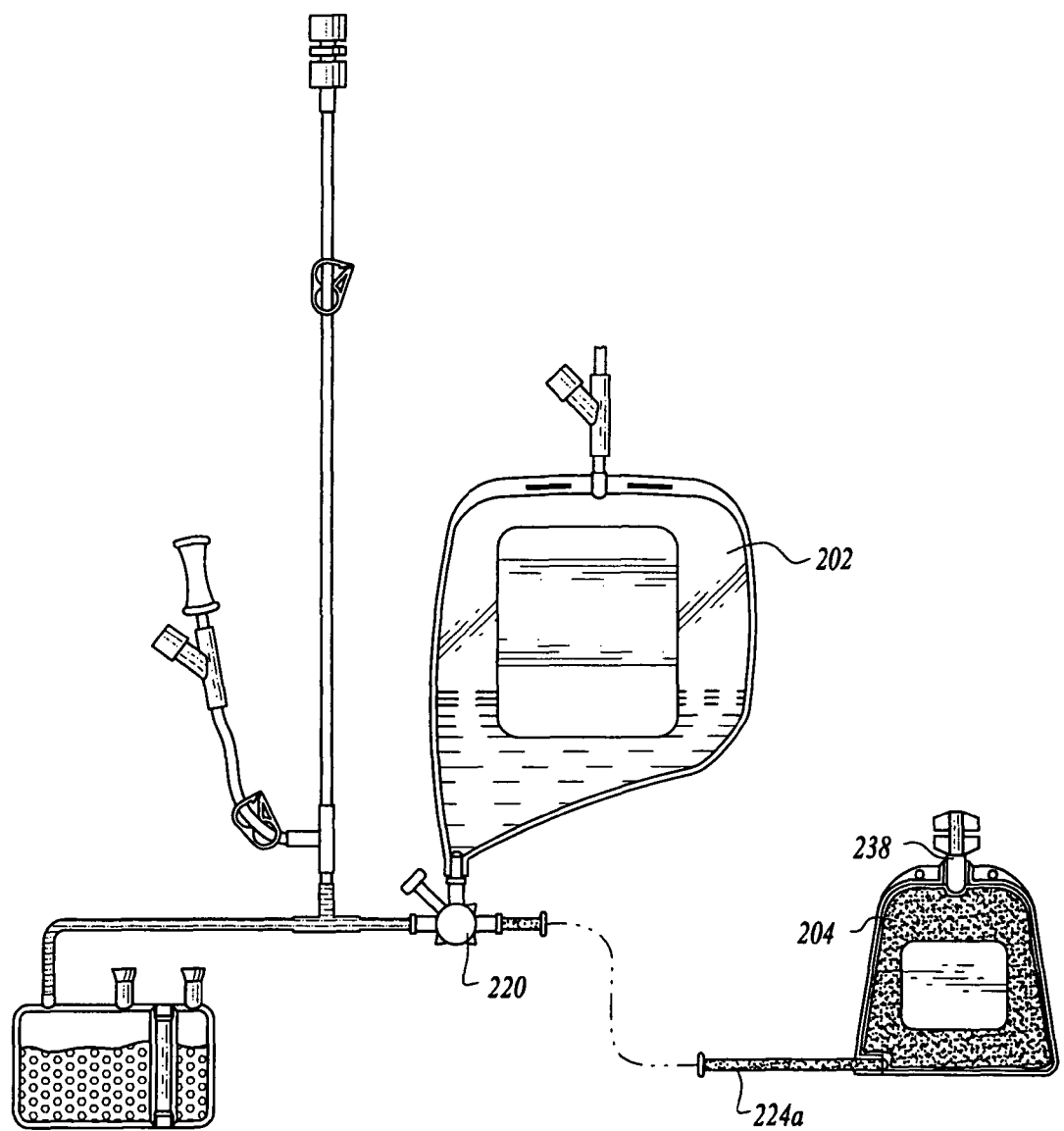
FIG. 24 shows the disconnection of the red blood cell bag from the bag set.

Unlike the prior art where a sedimentation agent is required, a sedimenting agent, such as hydroxyethyl starch (HES) may optionally be added to the processing bag 202 through the access port 236 on the inlet line 212 using syringe means 236a or similar delivery means, and the processing bag 202 is manipulated to thoroughly mix the agent with the blood (FIG. 21). The bag set 210 is then placed into the bag holder 50 and used with a centrifuge, as detailed hereinabove, to separate the cells therewithin (FIG. 22). The separated red blood cells are transferred into the RBC bag 204 and the WBC fraction is transferred to the freezing bag 206 during this operation. The bag set 210 is then removed from the bag holder 50 (FIG. 23). Supply line 224a is then heat sealed and the RBC bag 204 is removed (FIG. 24). The contents of the RBC bag are accessed through a sample port 238.

Figure 25:
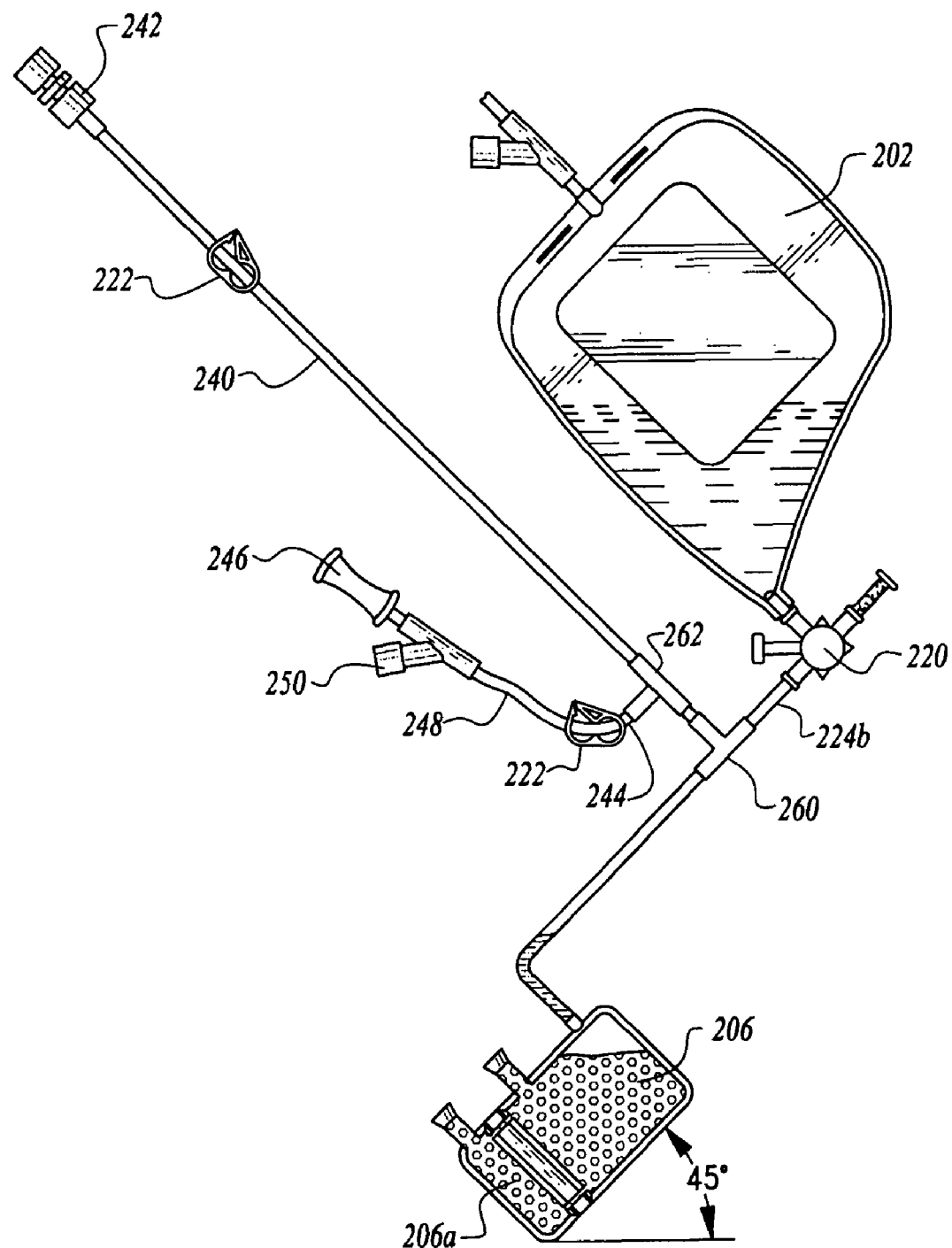
FIG. 25 illustrates the manner in which the contents of the freezing bag are mixed.

Referring to FIG. 25, supply line 224b is preferentially equipped with a first junction 260 connecting an auxiliary inlet line 240 terminating in an auxiliary port 242. A second junction 262 is present on the auxiliary inlet line 240 itself to connect a branch line 244 that terminates in a bulb 246. The branch line 244 also contains a sampling pigtail 248 and a sampling port 250. After removal of the RBC bag 204, the bulb 246 on the branch line 244 is squeezed to direct any residual plasma remaining in the supply line 224b into the freezing bag 206. Clamp 222 on branch line 244 is then closed. The contents of the freezing bag 206 are then mixed, preferably by holding the freezing bag 206 at a 45° angle and slowly squeezing the small compartment 206a of the freezer bag 206 a total of ten times at one squeeze per second.

Figure 26:
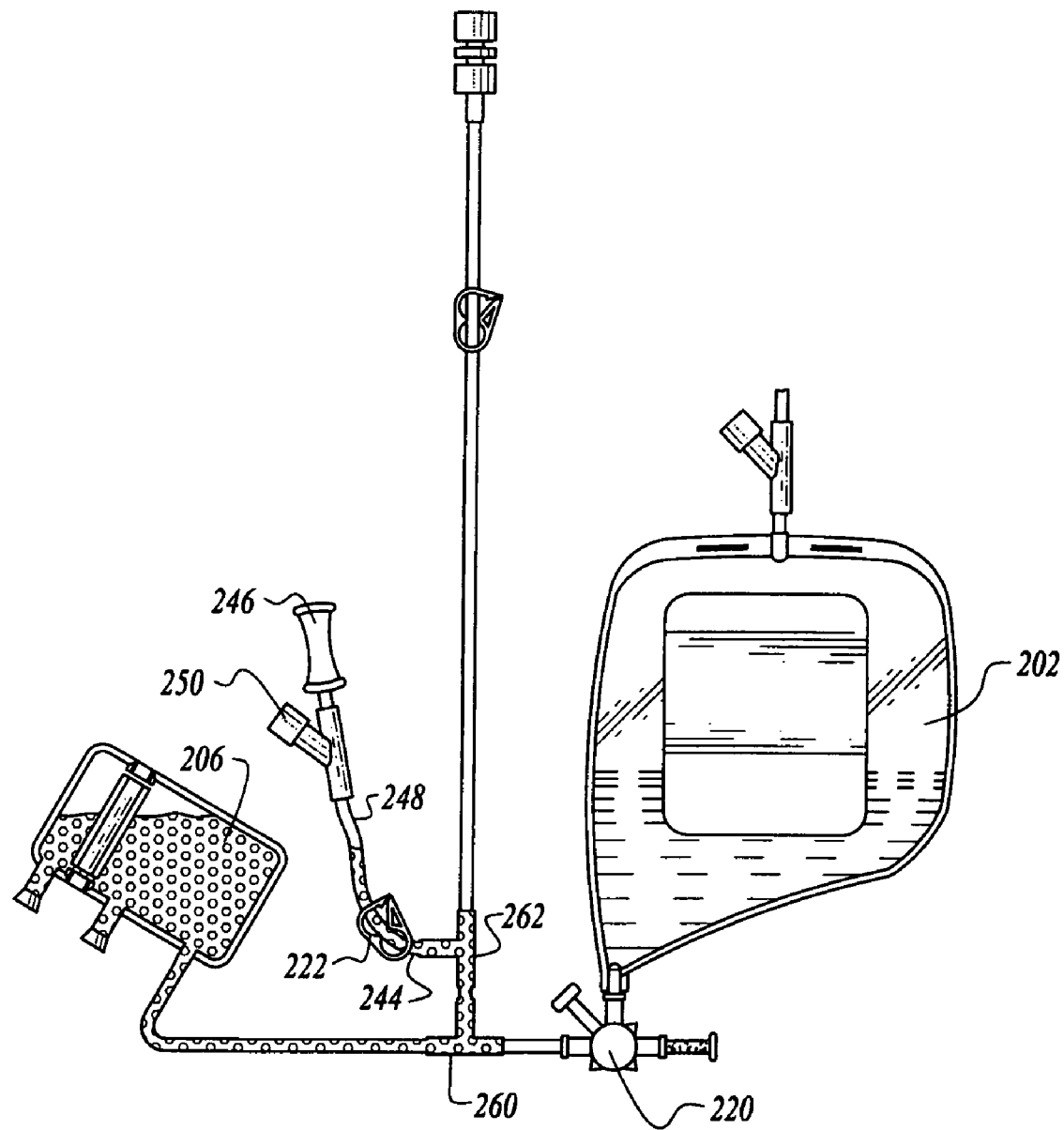
FIG. 26 depicts the process of filling the sampling pigtail with the contents of the freezing bag.
Figure 27:
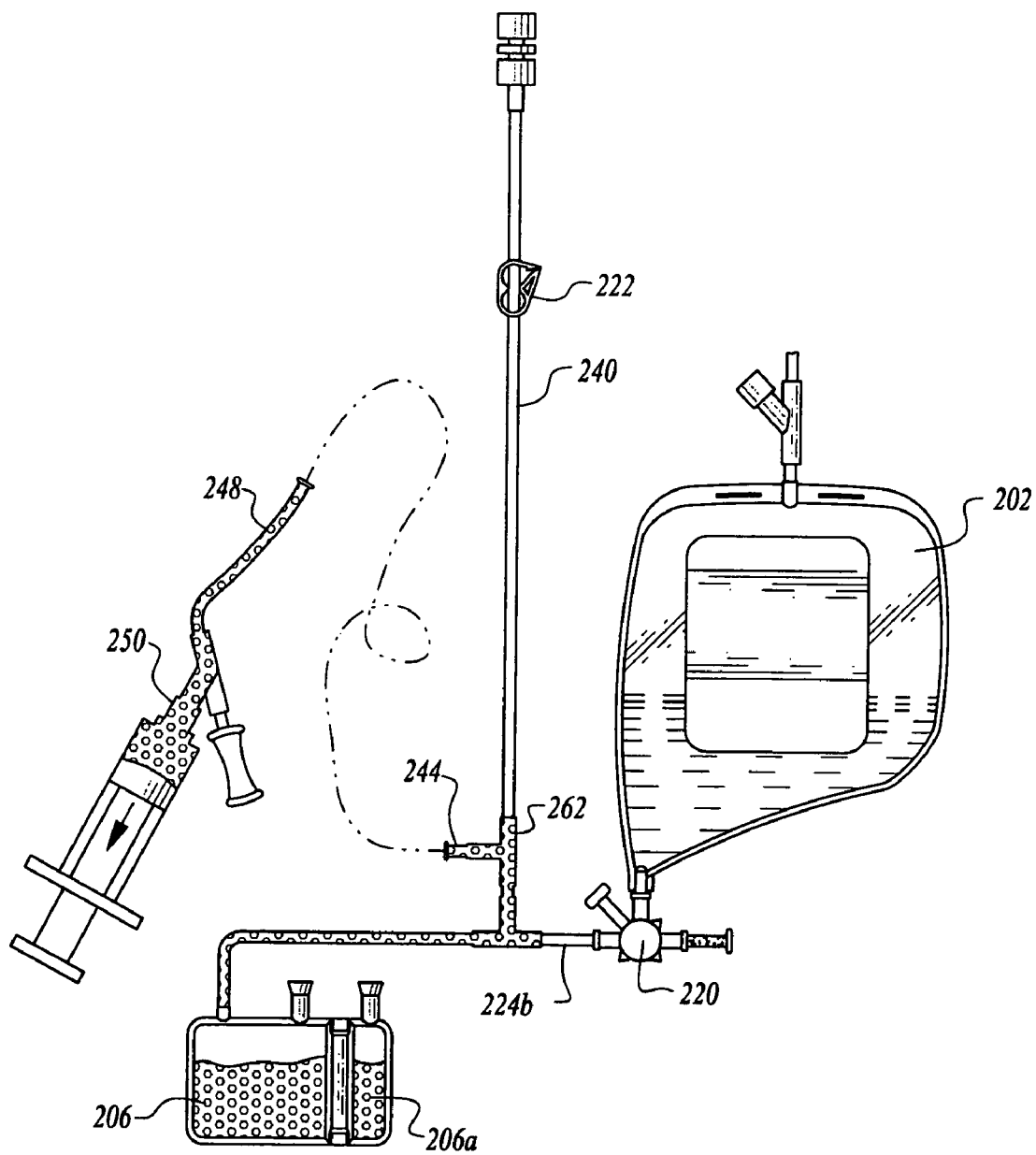
FIG. 27 shows the disconnection of the sampling pigtail and its associated sampling port from the bag set.

The clamp 222 on the branch line 244 is then opened, and the bulb 246 is squeezed and released to fill the sampling pigtail 248 with the contents of the freezer bag 206 (FIG. 26). The branch line 244 is heat sealed and removed from the bag set 210 (FIG. 27). The contents of the sampling pigtail 248 are accessed through the sampling port 250 for separate assay.

Figure 28:
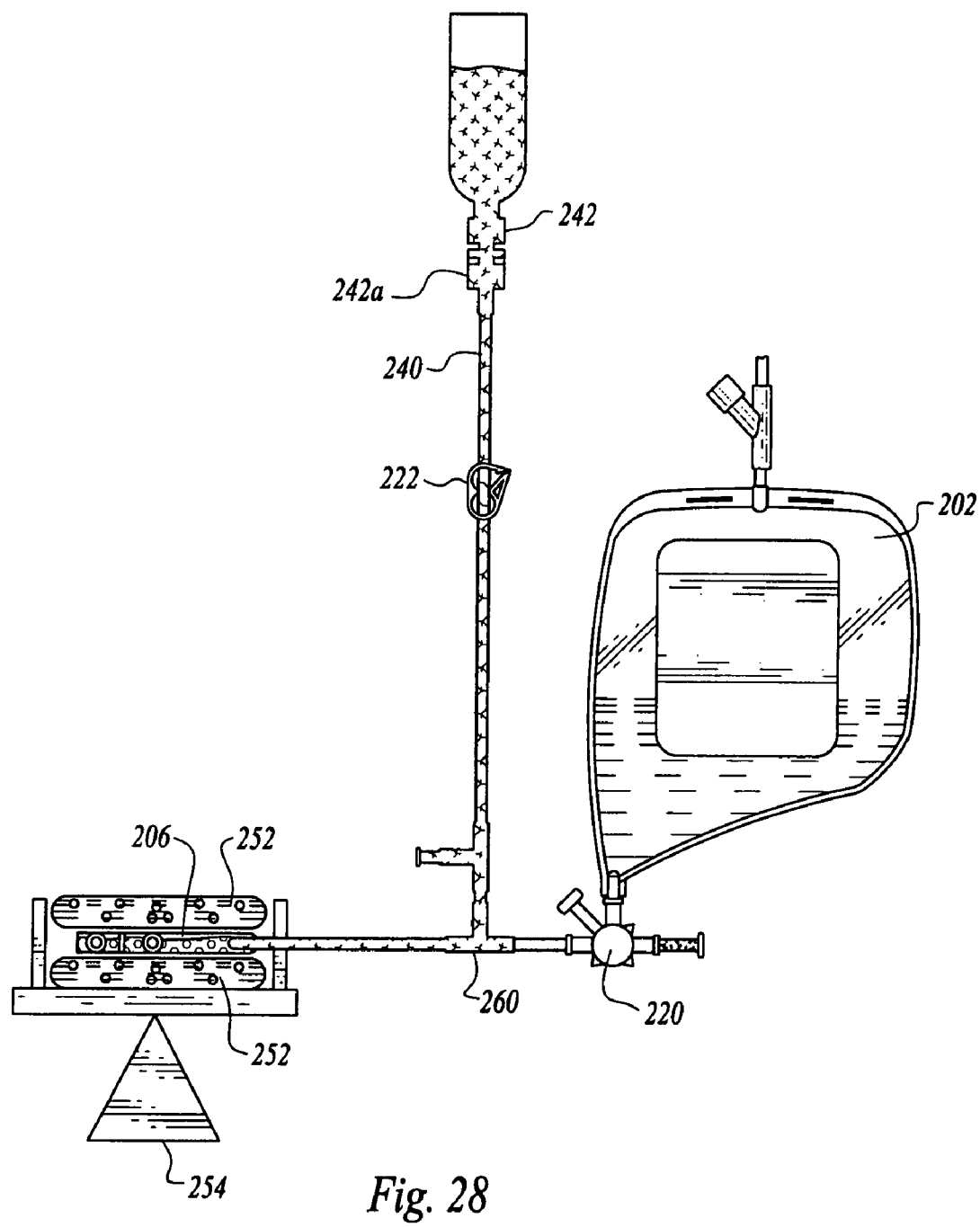
FIG. 28 depicts the addition of DMSO into the freezer bag and its subsequent mixing.
Figure 29:
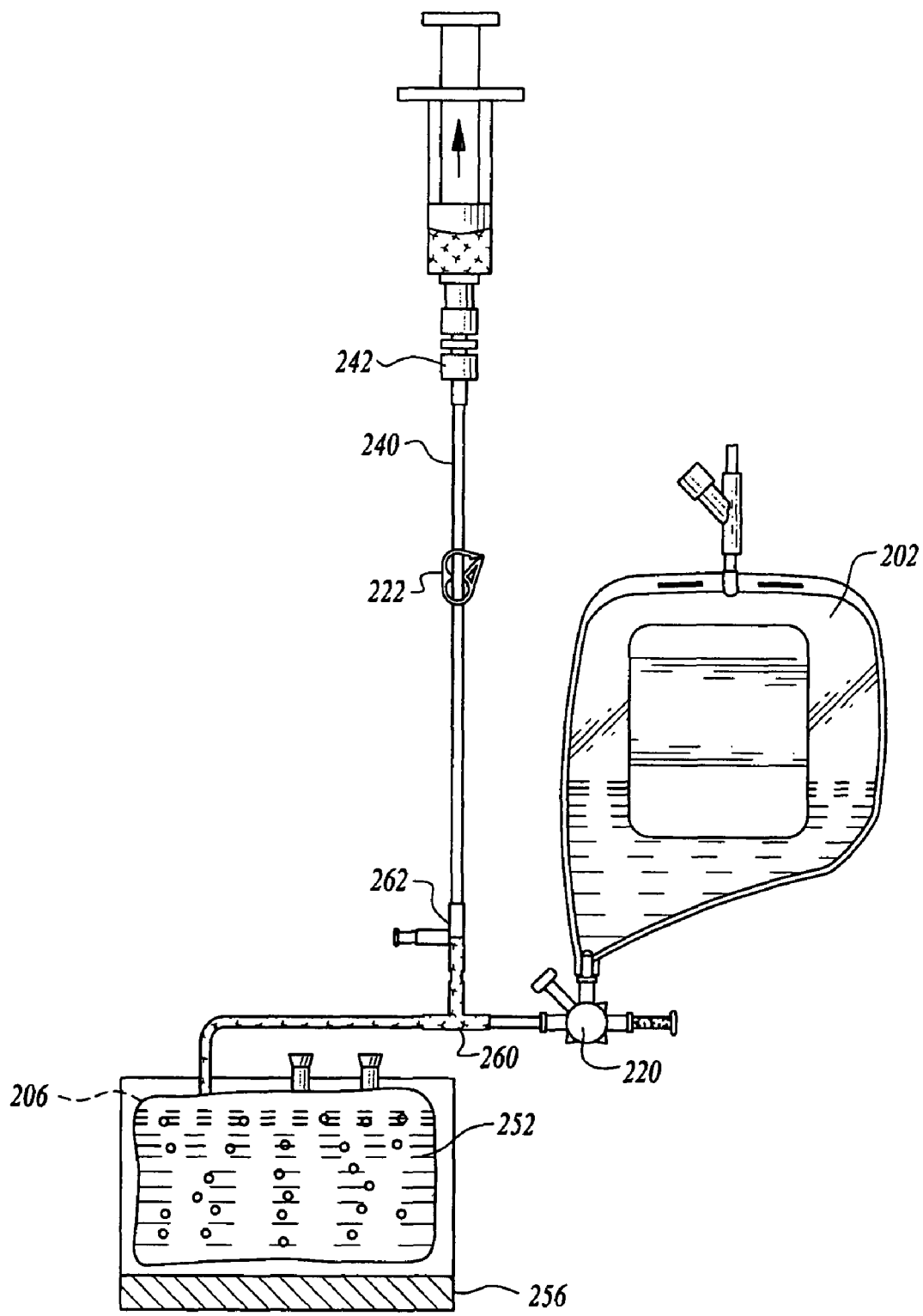
FIG. 29 illustrates the manner in which residual DMSO and air is drawn out of the system.
Figure 30:
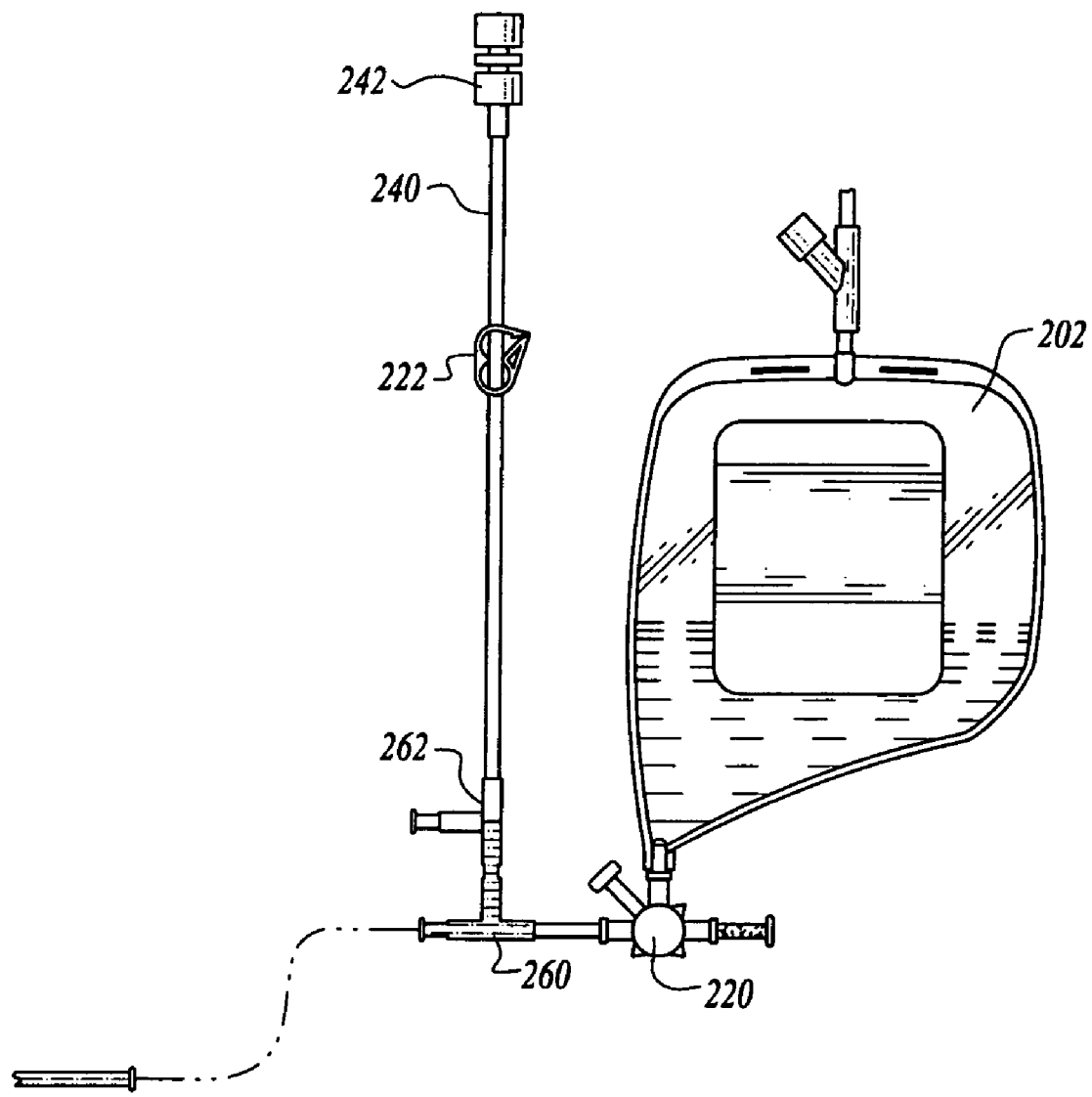
FIG. 30 shows the disconnection of the freezing bag from the bag set.

The freezing bag 206 is placed on its side and sandwiched between two ice packs 252 (FIG. 28). DMSO is introduced into the freezing bag 206 through the auxiliary port 242 which has a sterile filter 242a (i.e. less than or equal to 0.2 microns) on the auxiliary inlet line 240. An orbital mixer 254 is used with the sandwiched freezer bag 206 to thoroughly mix the contents of the freezer bag 206. The sandwiched freezer bag 206 is then placed in stationary holder 256 (FIG. 29). A syringe 258 is inserted into the auxiliary inlet 242 and used to draw out any residual DMSO and trapped air in the supply line 224b and the auxiliary inlet line 240. The buffy coat/ DMSO from the freezing bag 206 is drawn out by the syringe 258 until it reaches the second junction 262 from the supply line 224b. The freezing bag 206 is then removed from the bag set 210 by heat sealing the supply line 224b (FIG. 30).

Figure 31:
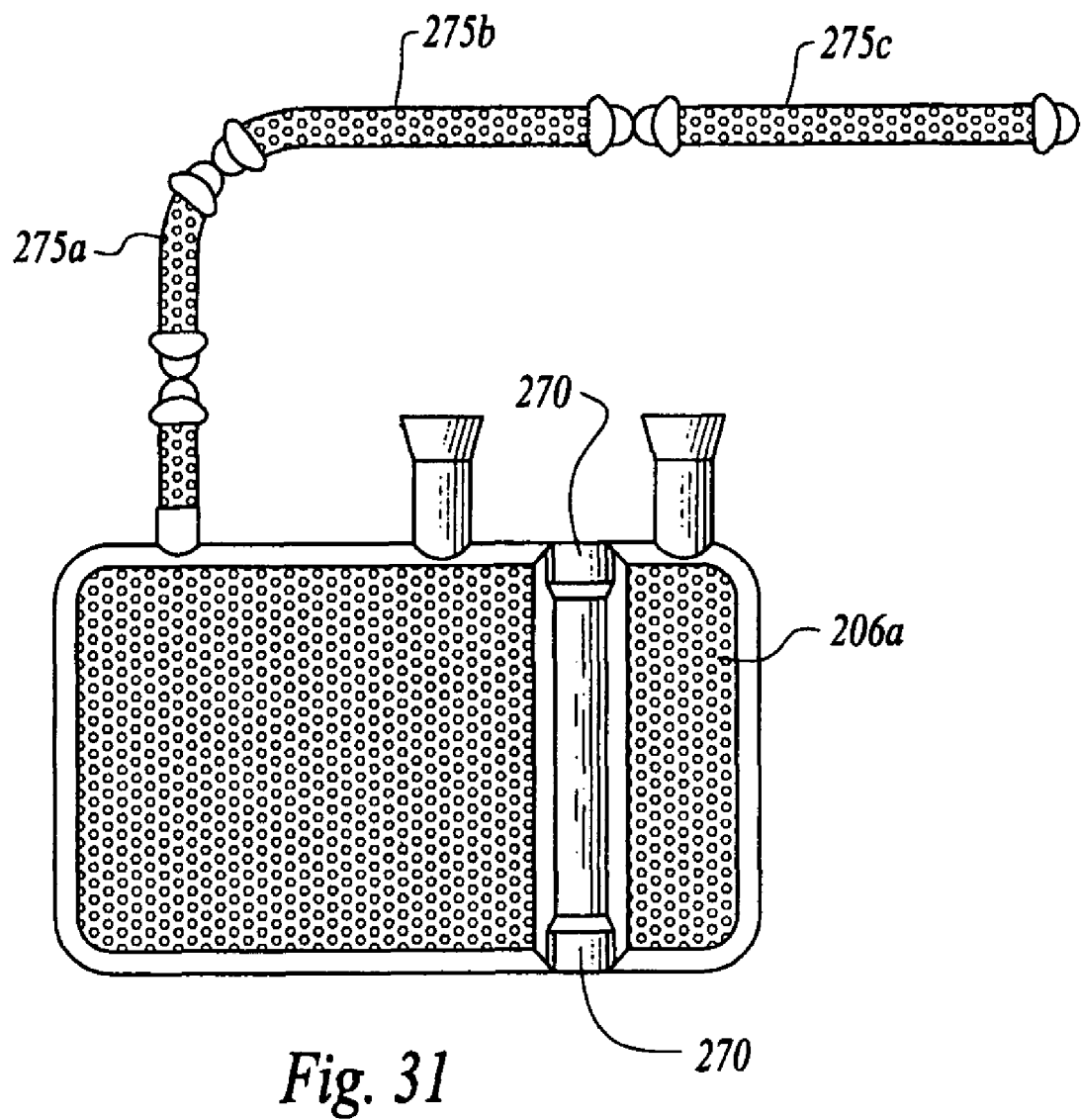
FIG. 31 illustrates the manner in which samples from the freezing bag portion are created for preservation.

A portion of the supply line 224b after the first junction 260 remains attached to the freezing bag 206. This portion of the supply line 224*b* is heat sealed to form three separate samples 275*a*,275*b*,275*c* (still connected to the freezing bag 206), and the area separating the small compartment 206*a* of the freezer bag 206 is heat sealed to separate it from the rest of the freezer bag 206 (FIG. 31). The final product is then frozen for storage.

Figure 32:
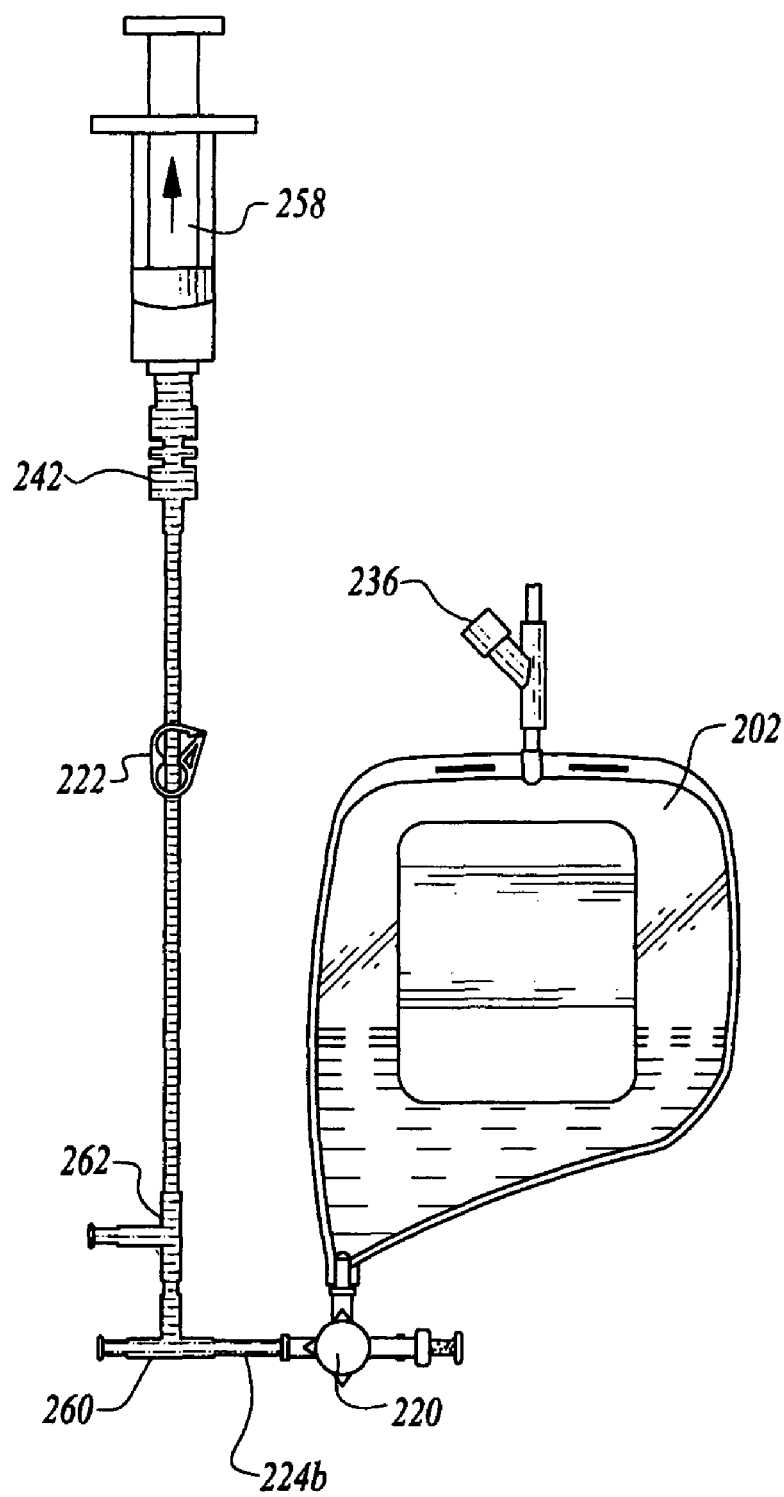
FIG. 32 shows the extraction of processing bag material and the small amount of freezing bag material left in the tubing from FIG. 31 for subsequent analysis.
Figure 33:
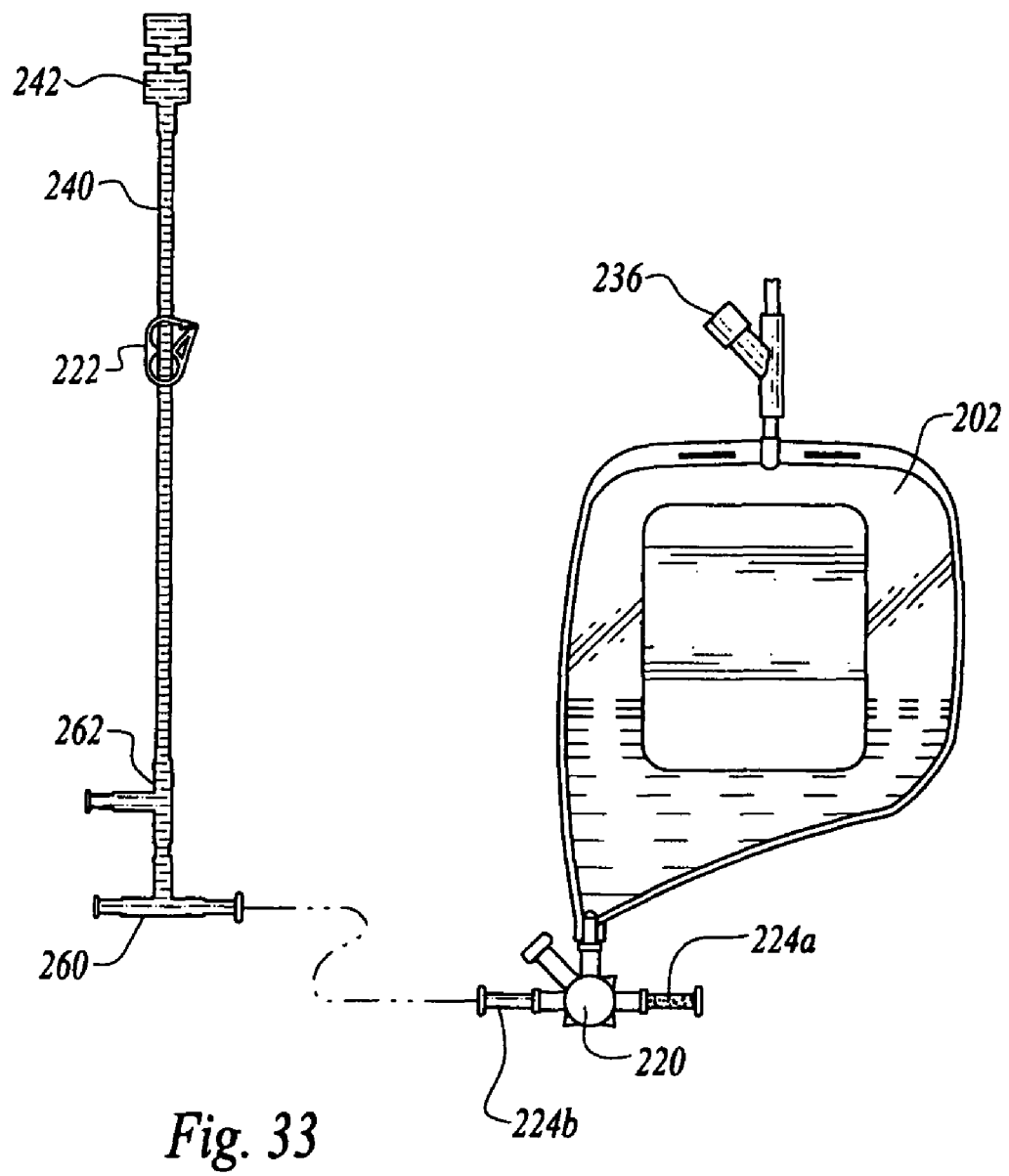
FIG. 33 shows the disconnection of the DMSO inlet line and its associated junctions from the processing bag.
Figure 34:
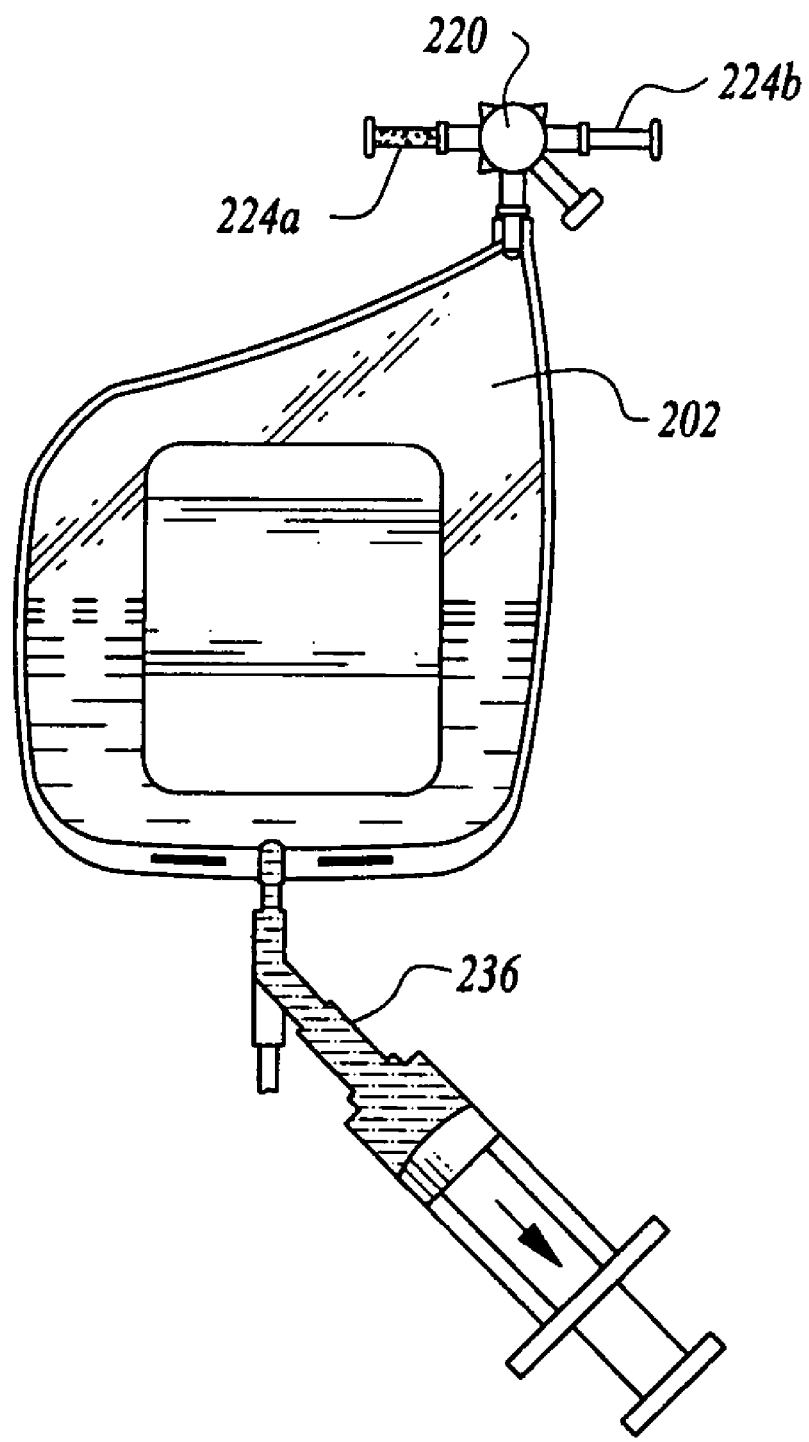
FIG. 34 illustrates the manner in which samples are taken from the processing bag for subsequent analysis.

The stopcock valve 220 is turned to allow plasma in the processing bag 202 to contact the buffy coat in the supply line 224*b* near the first and second junctions 260,262 (FIG. 32). A sample of the plasma diluted buffy coat is drawn into the syringe 258 for bacterial sampling, and the syringe 258 is removed from the auxiliary port 242. The supply line 224*b* containing the auxiliary line 240 and the first and second junctions 260,262 is then disconnected from the processing bag 202 and is discarded (FIG. 33). Samples of the plasma in the processing bag 202 may be removed by using the access port 236 (FIG. 34).

Moreover, having thus described the invention, it should be apparent that numerous structural modifications and adaptations may be resorted to without departing from the scope and fair meaning of the instant invention as set forth hereinabove and as described hereinbelow by the claims.

We claim:

1. An apparatus for use with a centrifuge to separate a liquid into components as a function of density, comprising, in combination:
   a housing having bag set support means, said housing having an exterior contour complemental to an interior bore of the centrifuge,
   a bag set defining a closed, sterile system said bag set including a processing bag having a liquid receiving inlet and an outlet under control of a valve, said valve selectively leading to plural other bags in said bag set,
   valve control means on said housing to direct liquid to said plural bags, and
   wherein said valve control means includes a scale means operatively coupled to one said plural bag to weigh liquid as it increases the weight of said one bag, said scale means and said valve control means operating in concert to precisely fill said one bag.

2. The apparatus of claim 1 wherein said valve control means includes a sensor strategically placed relative to said bag set and said housing to demark a transition in a liquid characteristic followed by a command to said valve to change orientation of said valve.

* * * * *